US009499780B2

(12) United States Patent
Smith et al.

(10) Patent No.: US 9,499,780 B2
(45) Date of Patent: Nov. 22, 2016

(54) ADVANCED TISSUE ENGINEERING SYSTEM

(75) Inventors: Timothy J. N. Smith, Kingston (CA);
Sydney M. Pugh, Calgary (CA);
Lowell Misener, Kingston (CA); Guy Oram, Kingston (CA); Rupert Hagg, Bassersdorf (CH);
(Continued)

(73) Assignee: OCTANE BIOTECH INC., Kingston, Ontario (CA)

( * ) Notice: Subject to any disclaimer, the term of this patent is extended or adjusted under 35 U.S.C. 154(b) by 1265 days.

(21) Appl. No.: 11/597,550

(22) PCT Filed: May 26, 2005

(86) PCT No.: PCT/CA2005/000783
§ 371 (c)(1),
(2), (4) Date: Oct. 11, 2007

(87) PCT Pub. No.: WO2005/116186
PCT Pub. Date: Dec. 8, 2005

(65) Prior Publication Data
US 2008/0113426 A1    May 15, 2008

Related U.S. Application Data

(60) Provisional application No. 60/574,223, filed on May 26, 2004.

(51) Int. Cl.
*C12M 1/00* (2006.01)
*C12M 3/00* (2006.01)
*C12M 1/12* (2006.01)

(52) U.S. Cl.
CPC ............. *C12M 23/34* (2013.01); *C12M 21/08* (2013.01); *C12M 23/44* (2013.01); *C12M 25/14* (2013.01); *C12M 45/09* (2013.01)

(58) Field of Classification Search
CPC .................. C12M 23/34; C12M 23/42; C12M 23/44; C12M 21/08; C12M 41/12; C12M 41/14; C12M 41/16; C12M 41/18
See application file for complete search history.

(56) References Cited

U.S. PATENT DOCUMENTS

| | | | |
|---|---|---|---|
| 6,238,908 B1 | 5/2001 | Armstrong et al. | |
| 7,348,175 B2 * | 3/2008 | Vilendrer et al. | 435/284.1 |
| 2002/0009803 A1 * | 1/2002 | Vajta | 435/325 |

(Continued)

FOREIGN PATENT DOCUMENTS

WO        03/087292 A2    10/2003

*Primary Examiner* — Nathan Bowers
(74) *Attorney, Agent, or Firm* — Aird & McBurney LP

(57) ABSTRACT

The invention is an automated advanced tissue engineering system that comprises a housing in which one or more tissue engineering modules are accommodated together with a central microprocessor that controls functioning of the tissue engineering modules. In one embodiment, the tissue engineering module comprises a housing supporting one or more bioreactor chamber assemblies and a fluid reservoir operationally engageable with the housing. The bioreactor chamber assemblies may be selected depending on the end product option desired and may include, for example, a cell therapy bioreactor chamber, a single implant bioreactor chamber and a multiple (mosaic) implant bioreactor chamber.

55 Claims, 19 Drawing Sheets

(75) Inventors: Roberto Tommasini, Uster (CH); Yves Larcher, Schlieren (CH)

(56) References Cited

U.S. PATENT DOCUMENTS

| | | | | |
|---|---|---|---|---|
| 2002/0037580 A1* | 3/2002 | Schoeb | .................... | 435/289.1 |
| 2003/0215935 A1* | 11/2003 | Coon | ........................ | 435/284.1 |
| 2005/0130297 A1* | 6/2005 | Sarem et al. | ............... | 435/297.1 |
| 2005/0186671 A1* | 8/2005 | Cannon et al. | ............ | 435/297.2 |

* cited by examiner

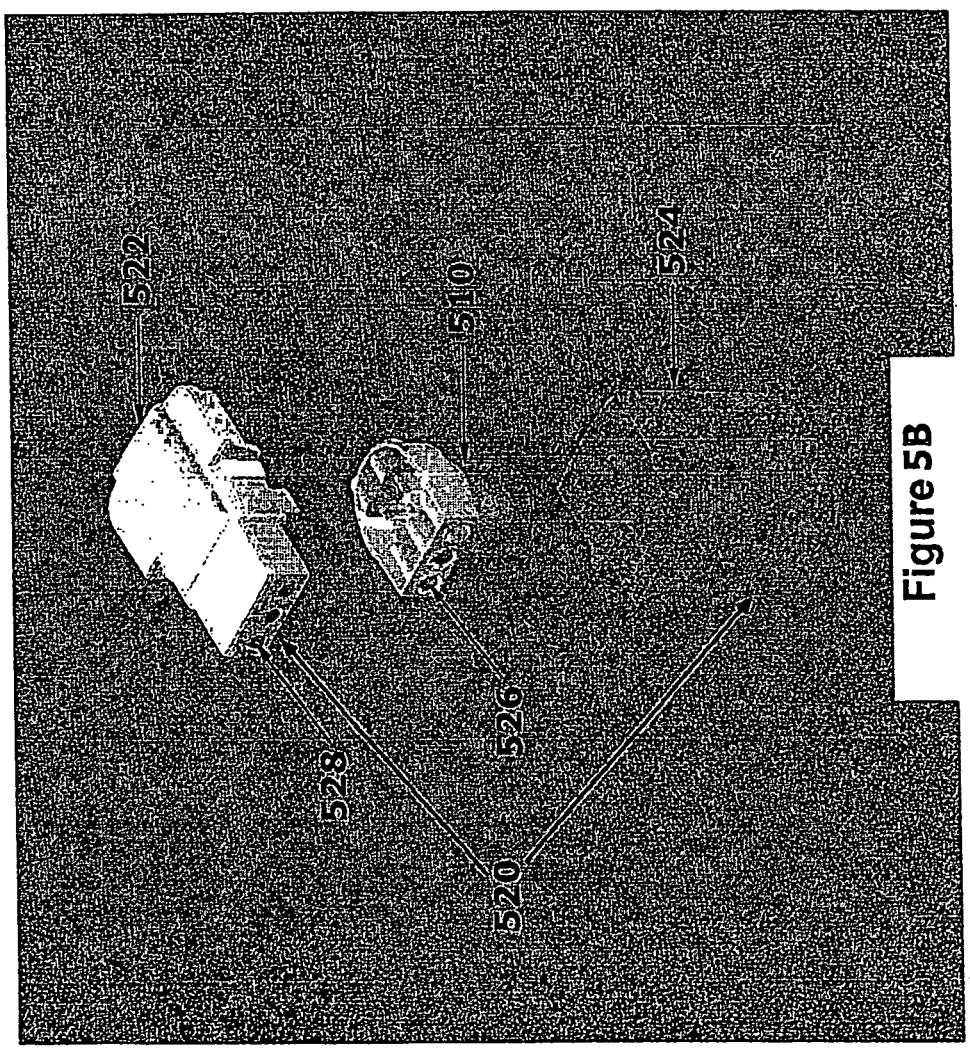

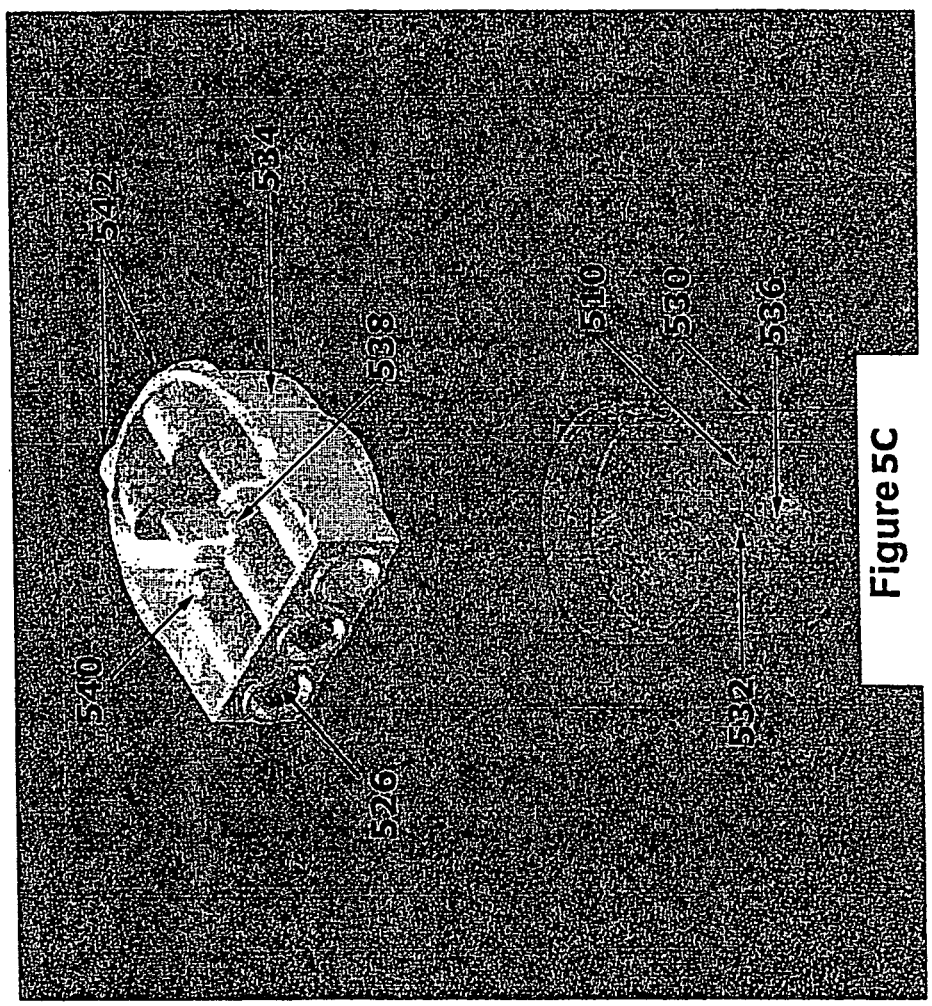

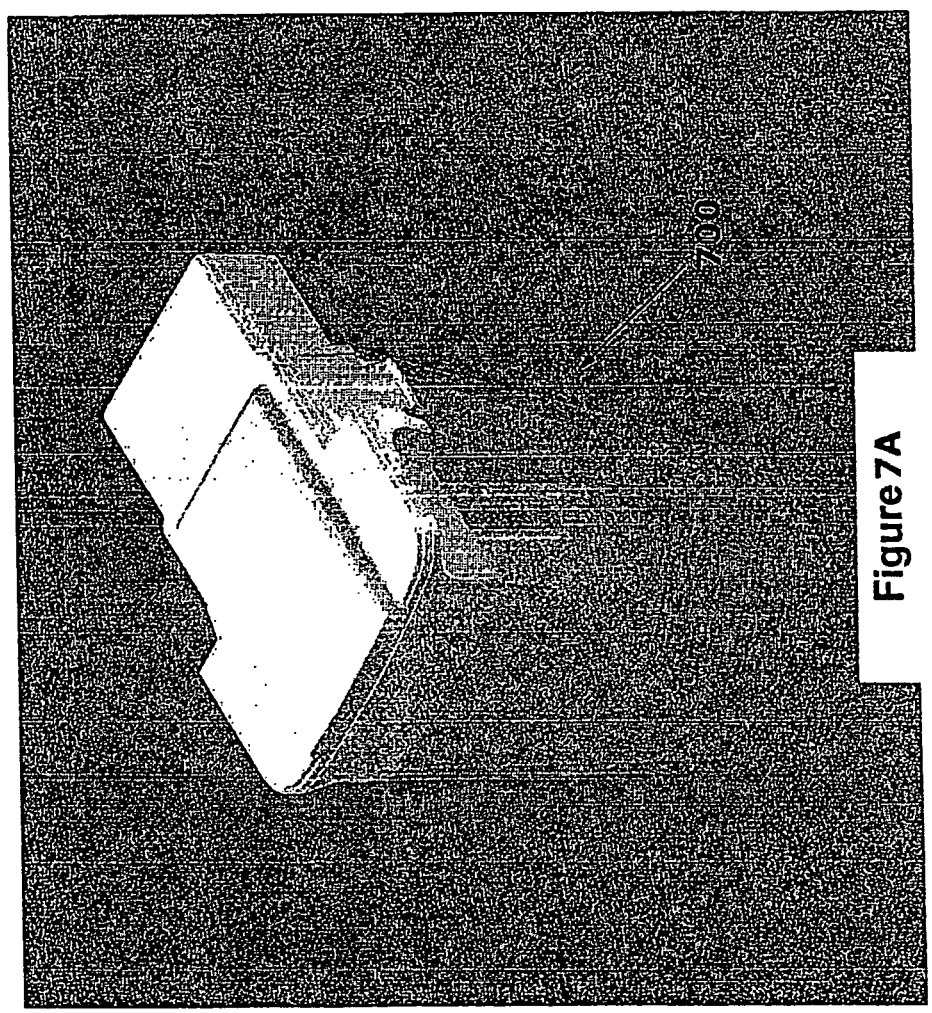

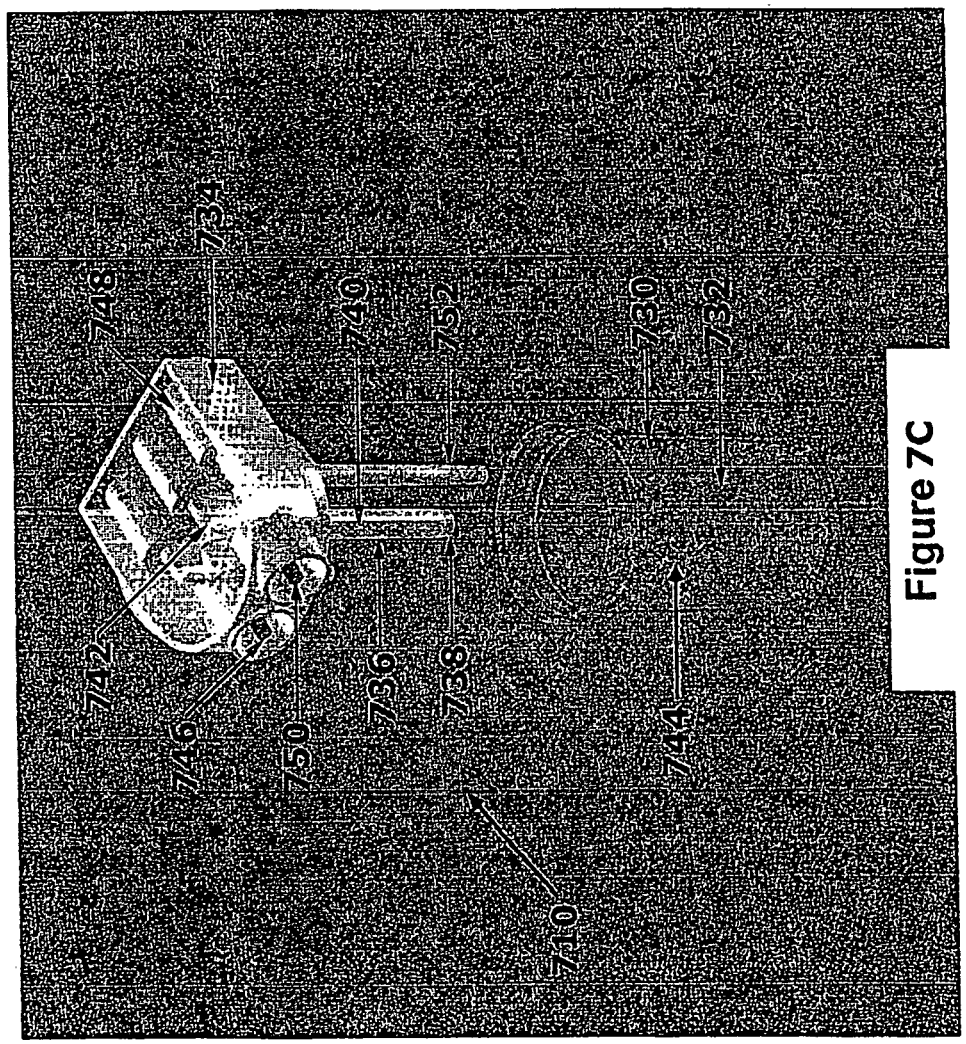

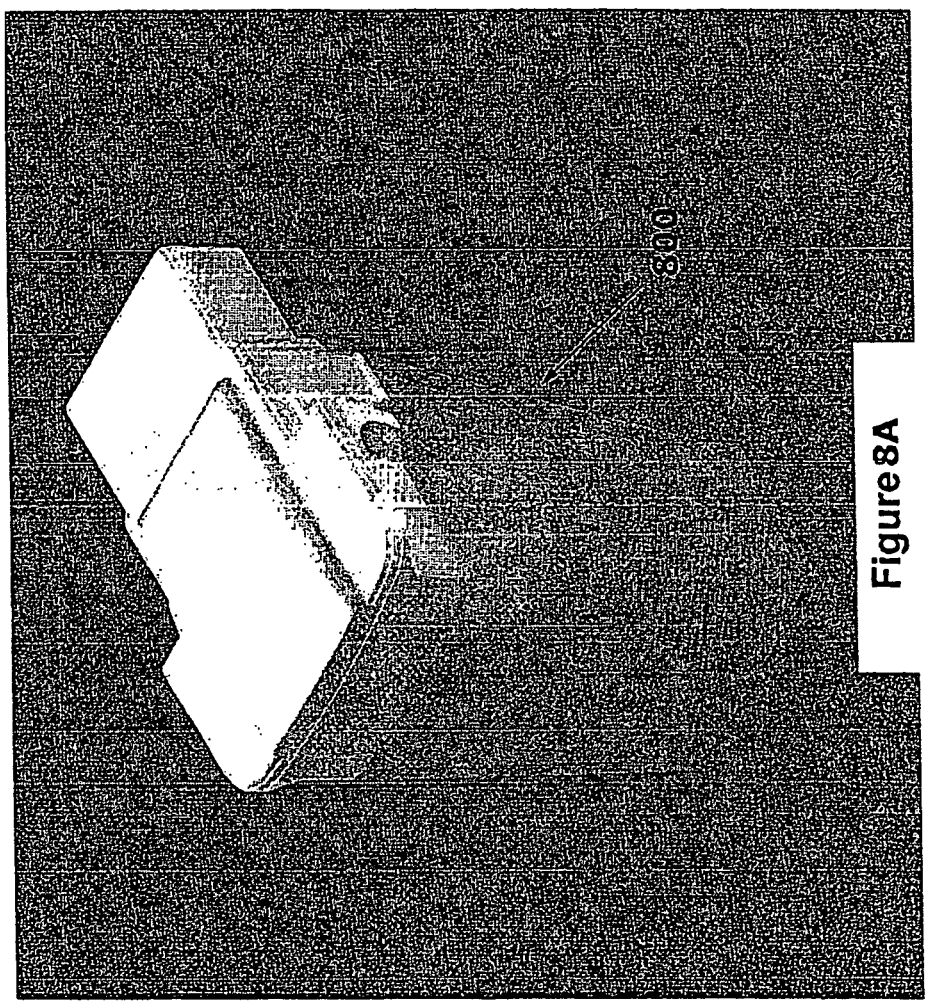

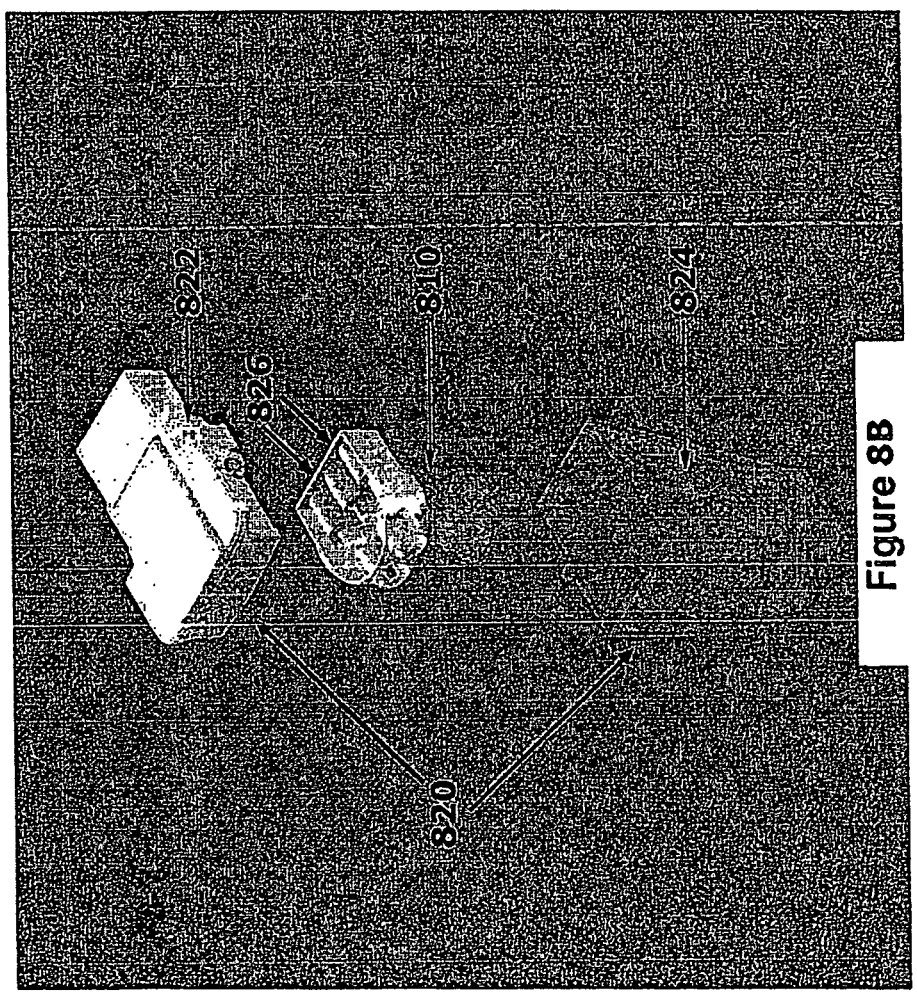

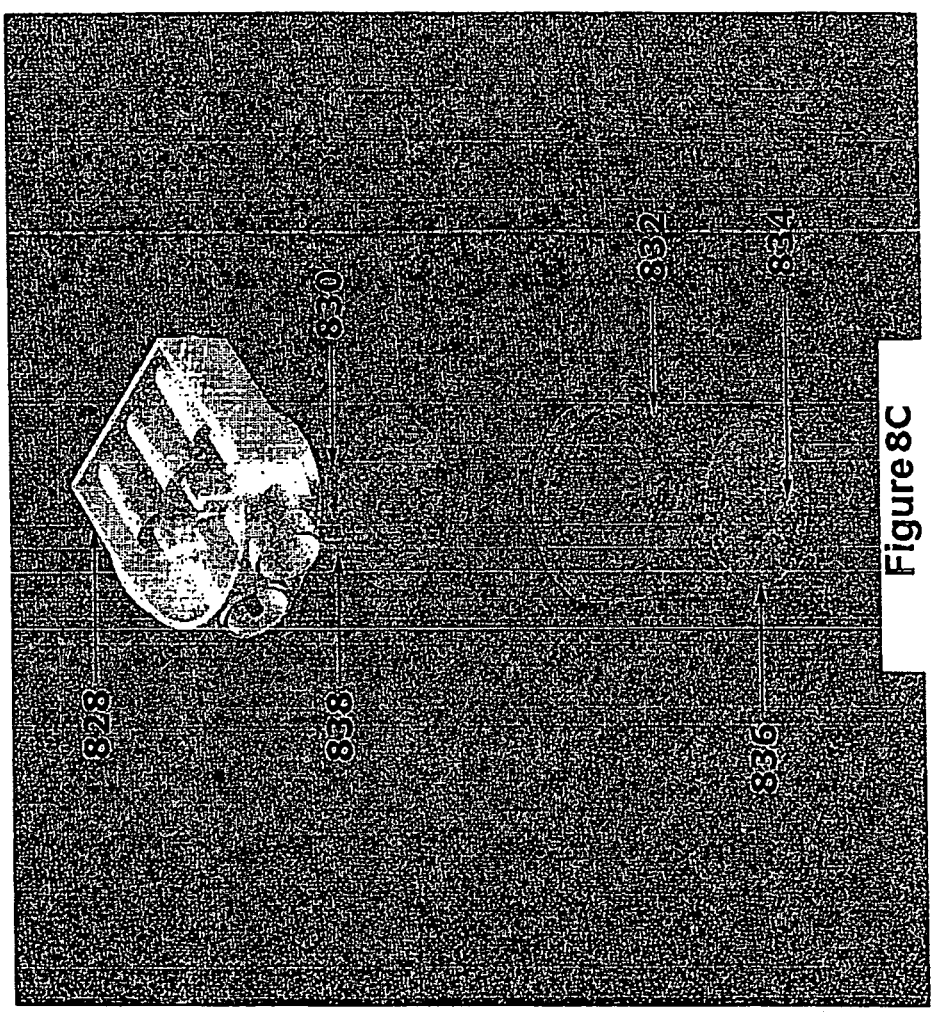

ADVANCED TISSUE ENGINEERING SYSTEM

RELATED APPLICATIONS

This application is a national phase entry of PCT/CA2005/00783 filed May 26, 2005 which claims the priority benefit of U.S. provisional application Ser. No. 60/574,223 filed on May 26, 2004 the disclosure of which is hereby incorporated by reference in its entirety.

FIELD OF THE INVENTION

The invention relates to a tissue engineering system. More specifically, the invention relates to an autologous advanced tissue engineering system for automated cell therapy and tissue engineering for clinical hospital settings.

BACKGROUND OF THE INVENTION

Different types of cell culture and tissue engineering devices have been developed as are described for example in U.S. Pat. Nos. 5,688,687, 5,792,603, 5,846,828, 5,994,129, 6,060,306, 6,048,721, 6,121,042, 6,228,635 and 6,238,908. The major drawbacks of these devices are the fact that they have limited functional capabilities and are useful only for the culture and expansion of cells. The devices are not designed for the production of autologous tissue implants. Furthermore, these devices are complex to use, bulky and thus not very portable, and still require user intervention in many aspects of the cell culturing process.

The Applicant has developed a fully automated tissue engineering system described in International Patent Application No. WO 03/0872292 (the disclosure of which is incorporated herein in its entirety). The system is a user-friendly and fully automated system for facilitating different physiological cellular functions and/or the generation of one or more tissue constructs from cell and/or tissue sources.

SUMMARY OF THE INVENTION

In one aspect, the present invention is an automated advanced tissue engineering system designed for further simplicity of use while maintaining aseptic conditions. The advanced tissue engineering system comprises a single housing operated by a central microprocessor unit that holds one or more tissue engineering modules that can be independently operated. The tissue engineering modules comprise a housing having one or more chamber assemblies and, in aspects, comprise a tissue digestion chamber assembly, a proliferation chamber assembly and a product chamber assembly. The product chamber assembly is selected based on the desired end use such as for cell collection for cell therapy or for various implant formation. The housing is operationally engageable to a separate fluid reservoir that, in one aspect, snaps onto the bottom of the housing. The tissue engineering module may also have a variety of biosensors to provide feedback with respect to the conditions within any of the chamber assemblies provided on the module as well as any fluids provided by the fluid reservoir and associated fluid tubing. Integrity sensors for monitoring that all parts are present and connected together correctly on the module may also be incorporated.

The advanced tissue engineering system can bring turn-key production capability for autologous cell therapy and tissue engineering to a hospital clinic. The system can be designed for ease-of-use while maintaining aseptic conditions. The system can avoid the inherent hazards and cost related to the transportation and centralized processing of human cells for various types of tissue repair and the advanced system can also provide for autologous, rather than allogenic or xenogenic sources of cells, tissue or serum.

According to an aspect of the present invention is an advanced automated tissue engineering system, the system comprising:
  a housing;
  one or more tissue engineering modules supported within the housing; and
  a central microprocessor that controls functioning of the one or more tissue engineering modules.

According to an aspect of the present invention is an advanced automated tissue engineering system, the system comprising:
  a housing;
  one or more tissue engineering modules supported within the housing;
  at least one biosensor associated with the housing and/or the one or more tissue engineering modules; and
  a central microprocessor that controls functioning of the one or more tissue engineering modules.

According to another aspect of the present invention is a network of automated tissue engineering systems, wherein at least one of the automated tissue engineering systems is the automated tissue engineering system of present invention.

In aspects of the invention, the central microprocessor unit (CPU) of the system is used to programme and control the functioning and operation of the entire system and the tissue engineering module(s) contained therein. For example, the CPU is used to release the tissue engineering module using an automatic sequence triggered by a user command on the touch screen display.

According to another aspect of the present invention is a tissue engineering module comprising:
  a housing supporting at least one chamber assembly, the at least one chamber assembly selected for at least one of tissue digestion, cell proliferation, cell differentiation and implant formation;
  a fluid reservoir operationally engageable with the housing; and
  at least one biosensor for the monitoring of parameters within at least one of the fluid reservoir and the at least one chamber assembly.

According to another aspect of the present invention is a tissue engineering module, the module comprising:
  a housing supporting a number of chamber assemblies selected for tissue digestion, cell proliferation, cell differentiation and/or implant formation;
  a fluid reservoir operationally engageable with the housing; and
  at least one biosensor for the monitoring of parameters within the chamber assemblies and/or within the fluid reservoir.

According to another aspect of the present invention is a tissue engineering module, the module comprising;
  a housing supporting a tissue digestion chamber assembly, a proliferation chamber assembly and a product chamber assembly;
  a fluid reservoir connected to the housing and in fluid communication with the tissue digestion chamber assembly, the proliferation chamber assembly and the product chamber assembly; and
  at least one biosensor associated with one or more of the fluid reservoir, the tissue digestion chamber assembly, the proliferation chamber assembly and the product chamber assembly, the at least one biosensor being in communication with a remote central processor.

According to yet another aspect of the present invention is a tissue engineering module, the module comprising;
   a housing, the housing supporting a removable tissue digestion chamber assembly, a fixed proliferation bioreactor and a removable product chamber assembly;
   a fluid reservoir connected to the housing and in fluid communication with the tissue digestion chamber assembly, the proliferation bioreactor and the product chamber assembly; and
   at least one biosensor associated with one or more of the fluid reservoir, the tissue digestion chamber assembly, the proliferation bioreactor and the product chamber assembly, the at least one biosensor being in communication with a remote central processor.

In aspects, the tissue engineering module is capable of conducting at least one of tissue digestion, cell proliferation, cell differentiation and implant formation; individually, sequentially, predetermined sequences or partial sequences.

In aspects, the product chamber assembly is configured depending on the end product option desired and may be selected to include for example a cell therapy bioreactor that collects and holds proliferated cells for cell therapy applications; and a differentiation bioreactor for the differentiation of cells into either a single implant, multiple (mosaic) implant or a cell matrix implant.

According to yet another aspect of the present invention is a tissue digestion chamber assembly, the assembly comprising:
   a protective containment unit comprising a unit lid and a unit base; and
   a tissue digestion bioreactor within the protective containment unit.

According to still another aspect of the present invention is a tissue digestion chamber assembly, the assembly comprising:
   a protective containment unit comprising a unit lid and unit base; and
   a tissue digestion bioreactor supported within the protective containment unit.

In aspects, the tissue digestion chamber assembly is portable and can be mounted within a tissue engineering module. The tissue digestion chamber assembly is primarily for the digestion of patient biopsy material to retrieve cells for further proliferation, differentiation and/or implant formation. However, the tissue digestion chamber can also be used in aspects to directly receive patient cells without the need for any digestion.

According to yet another aspect of the present invention is a proliferation chamber assembly, the assembly comprising:
   a proliferation bioreactor comprising a proliferation chamber having a base, a lid for containment of fluid, and a channel system therein.

According to still another aspect of the present invention is a proliferation chamber assembly, the assembly comprising:
   a proliferation bioreactor comprising a substantially flat base with a large surface area, the base having a channel system therein for flow of medium and cells; at least one biosensor to detect and provide feedback on the condition of cell culture and proliferative activity; and a lid to provide a chamber for containment of fluid.

In aspects of the invention, the proliferation bioreactor is mounted within a housing of a tissue engineering module. This mounting may in aspects be fixed. The proliferation bioreactor may also in aspects comprise a gas permeable membrane, flow interrupters, and vibratory elements. In other aspects, the proliferation bioreactor may be provided having one or more bases stacked on top of one another to provide additional surface area for the proliferation of cells. The base(s) may also be mounted within the bioreactor at an angle to provide an elevational change from inlet to outlet.

According to another aspect of the present invention is a product chamber assembly, the assembly comprising:
   a protective containment unit comprising a unit lid and a unit base; and
   a product bioreactor within the protective containment unit.

According to yet another aspect of the present invention is a product chamber assembly, the assembly comprising:
   a protective containment unit comprising a unit lid and a unit base; and
   a product bioreactor supported within the protective containment unit.

According to still another aspect of the present invention is a product chamber assembly, the assembly comprising:
   a protective containment unit comprising a unit lid and unit base; and
   a differentiation bioreactor supported within the protective containment unit.

In aspects, the differentiation bioreactor is configured for the collection of cells, for the generation of one or more implants, or for the generation of cell matrix implant. In aspects of the invention, the product chamber assembly can be reversibly mounted to a tissue engineering module.

In other aspects of the invention, any one of the chamber assemblies can be engageable with a tissue engineering module. This can be done in a reversible manner or in an irreversible manner with any of the assemblies as desired. For example, it may be desirable in aspects to have the tissue digestion chamber assembly non-removable after initial installation to ensure that the digest bioreactor is not re-used. By default, this ensures that the remainder of the tissue engineering module cannot be re-used.

It is noted that although the tissue engineering module is shown to have a tissue digestion chamber assembly, a proliferation chamber assembly and a product chamber assembly, not all of these assemblies need to be used to create a final end product for clinical use. As a non-limiting example, cells provided by enzymatic digestion of a surgical biopsy in the tissue digestion chamber assembly can be moved either to the proliferation chamber assembly or directly to the product chamber assembly.

According to yet another aspect of the present invention is a tissue engineering module comprising at least one of the tissue digestion chamber assembly, the proliferation chamber assembly, and the product chamber assembly of described herein.

According to another aspect of the present invention is a tissue engineering module comprising:
   a housing supporting a fluid reservoir and at least one of the tissue digestion chamber assembly, the proliferation chamber assembly, and the product chamber assembly of described herein; and
   at least one biosensor for the monitoring of parameters within at least one of the fluid reservoir and said at least one chamber assembly.

Other features and advantages of the present invention will become apparent from the following detailed description and drawings. It should be understood, however, that the detailed description and drawing while indicating embodi-

BRIEF DESCRIPTION OF THE DRAWINGS

FIG. 5B shows a partial exploded view of the tissue digestion bioreactor assembly of FIG. 5A showing a protective unit lid, a tissue digestion bioreactor, and a unit base;

FIG. 5C shows a partial exploded view of the tissue digestion bioreactor of FIG. 5B;

FIG. 7A shows a perspective view of one embodiment of a product chamber assembly of the present invention;

FIG. 7C shows a partial exploded view of the differentiation bioreactor of FIG. 7B;

FIG. 8A a perspective view of another embodiment of a product chamber assembly of the present invention;

FIG. 8B shows a partial exploded view of the product chamber assembly of FIG. 8A showing a protective unit lid, a cell therapy bioreactor, and a unit base;

FIG. 8C shows a partial exploded view of the cell therapy bioreactor of FIG. 8B;

DETAILED DESCRIPTION OF THE INVENTION

The present invention is an improvement to the Applicant's automated tissue engineering system described in International Patent Application No. WO 03/0872292 (the disclosure of which is incorporated herein in its entirety). The advanced automated tissue engineering system of the invention has a variety of improvements incorporated therein in order to increase the ease-of-use, maintain the aseptic conditions of the system and simplify the manufacture of the system, yet basically operates in the same manner as the system of Applicant's International Patent Application No. WO 03/0872292.

Figure 1:
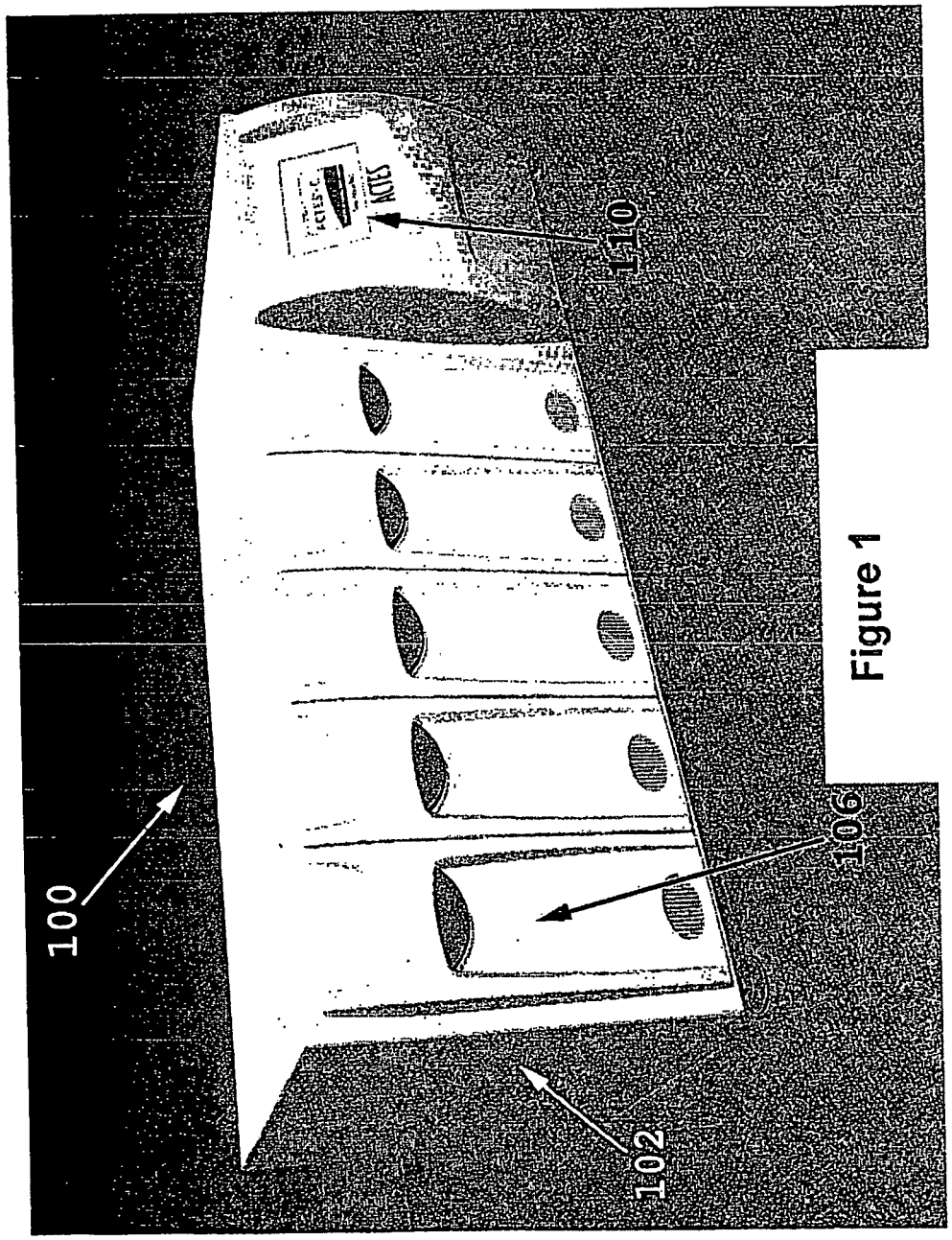
FIG. 1 shows a perspective view of an advanced tissue engineering system of one embodiment of the present invention.
Figure 2:
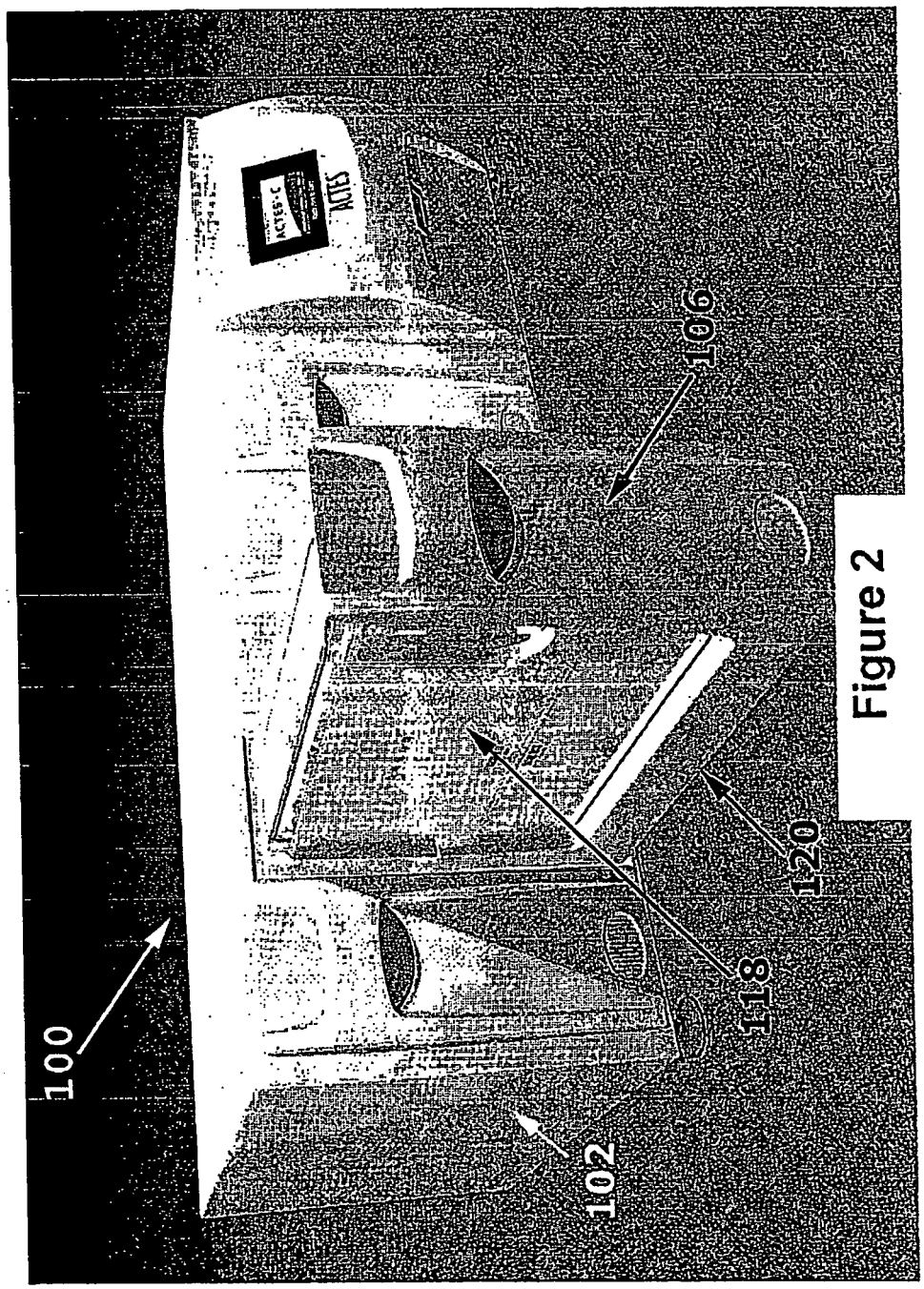
FIG. 2 shows the advanced tissue engineering system of FIG. 1 with one of the bay doors in the open position.

The present invention will now be described in more detail with reference to the Figures. FIG. 1 shows the advanced tissue engineering system 100. The system comprises a housing 102, multiple bays 106 each accommodating a tissue engineering module (not shown) and a user interface touch screen 110. FIG. 2 shows the tissue engineering system 100 with one of the bays 106 and the associated door in the open position. The automated insertion and retraction system is supported by a guide rail system 120. Each of the bays can contain one tissue engineering module 118 which is secured to the bay by automated latches residing in the bay (not shown) and can be programmed to be removed through the entry of a specific password via the touch screen to prevent unauthorized or unscheduled access or tampering.

Figure 3:
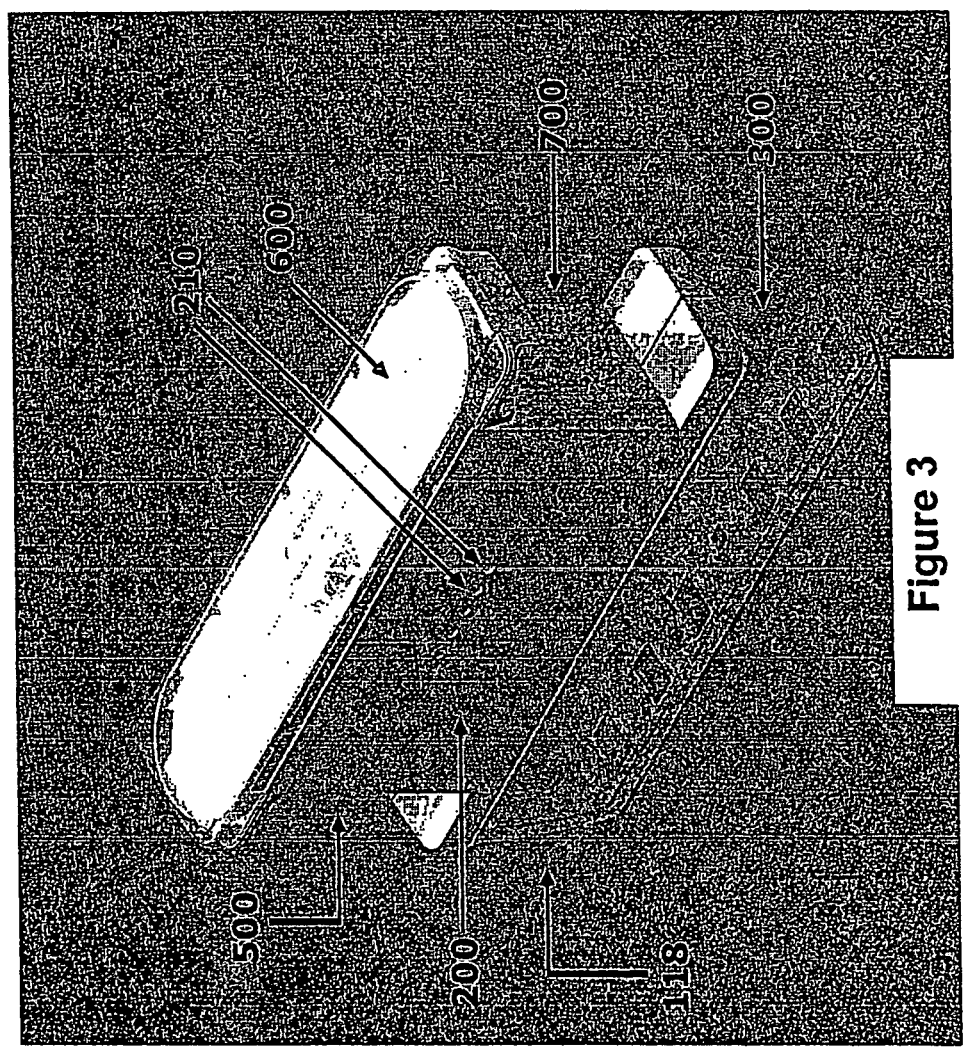
FIG. 3 shows a perspective view of one side of an embodiment of a tissue engineering module of the present invention removed from the bay door of FIG. 2.
Figure 4:
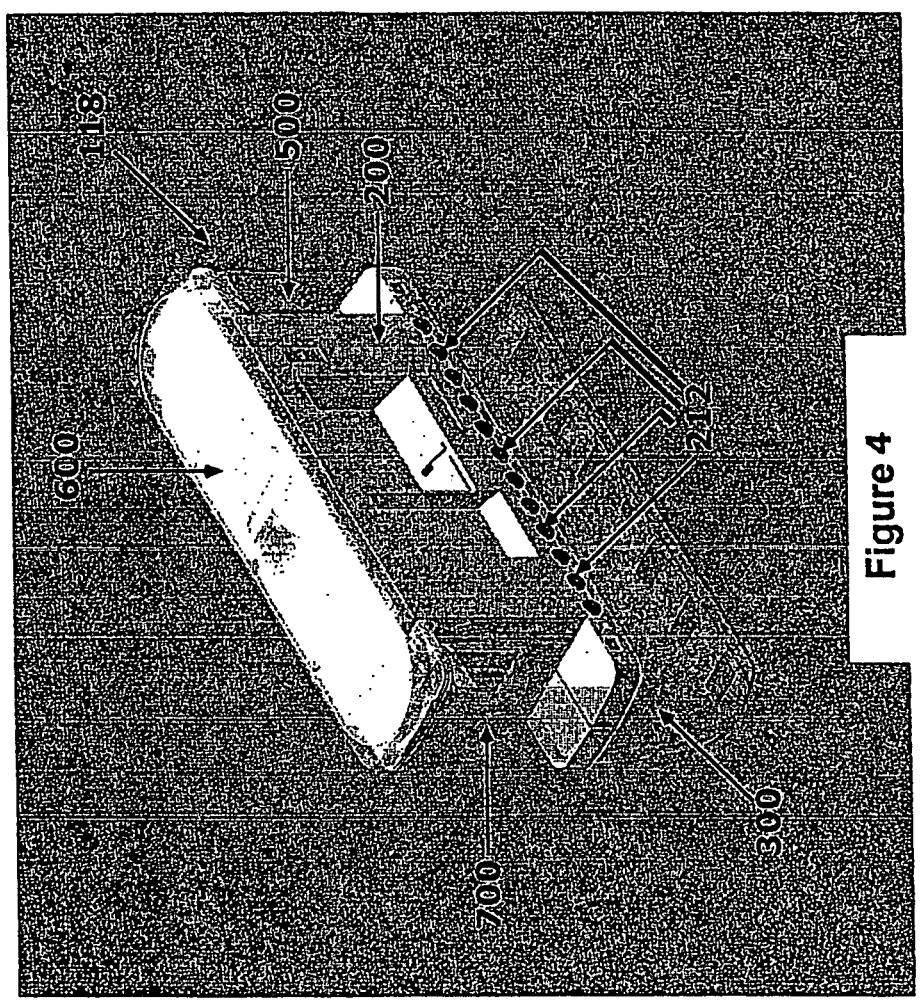
FIG. 4 shows a perspective view of the other side of the tissue engineering module of FIG. 3.

FIGS. 3 and 4 show two side perspective views of the assembled tissue engineering module 118 removed from the bay. The module 118 has two main components; the upper housing 200 and the lower fluid reservoir 300. The upper housing 200 has a tissue digestion chamber assembly 500, a proliferation chamber assembly 600, and a product chamber assembly 700. There are fluid access ports 210 located on one side of the module 118 and internally connected to the fluid pathway (not shown) within the module 118, which can be used for quality control sample removal and component addition to the internal fluid system if required. There are flow control valves 212 located on the other side of the module 118.

The chamber assemblies 500, 600 and 700, the lower fluid reservoir 300, and the remainder of the module 118 are each described below, respectively.

Figure 5A:
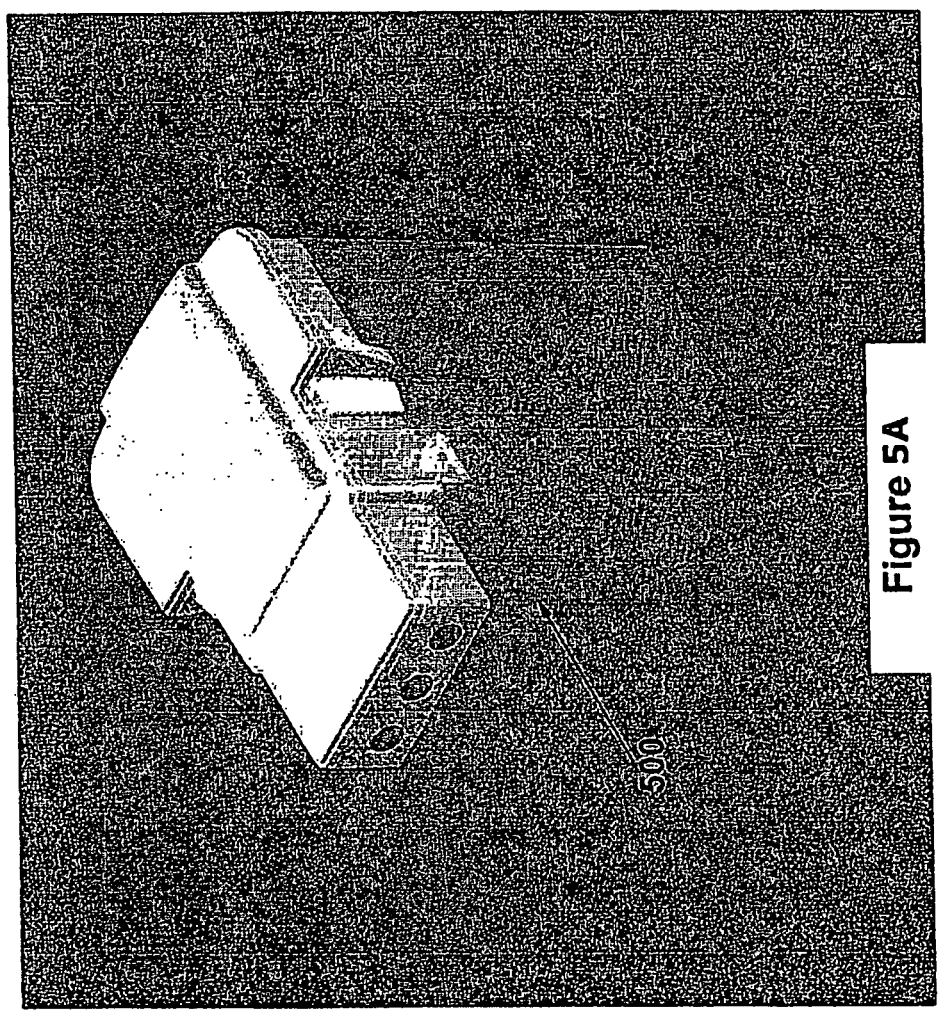
FIG. 5A shows a perspective view of one embodiment of a tissue digestion chamber assembly of the present invention.

FIG. 5A shows the tissue digestion chamber assembly 500. FIGS. 5B and 5C illustrate the components of the tissue digestion chamber assembly 500. The chamber assembly 500 comprises a tissue digestion bioreactor 510, described more fully with respect to FIG. 5C, and an outer protective containment unit 520. The outer protective containment unit 520 comprises a protective unit lid 522 and a unit base 524 to enhance the protection and isolation of the contents of the bioreactor 510 therein. The tissue digestion bioreactor 510 is connected to the protective unit lid 522 via sterile needleless connectors 526. Each of the connectors 526 is in direct fluid communion with a corresponding mating connector 528 of the protective unit lid 522. Once the tissue digestion bioreactor 510 is connected to the protective unit lid 522, the protective unit lid 522 is then connected to the unit base 524.

The tissue digestion bioreactor 510 shown in FIG. 5C has four primary components: a bioreactor base 530 that substantially forms a tissue digestion chamber 532 of an appropriate size to accommodate one or more tissue samples such as a tissue biopsy (not shown); a removable bioreactor lid 534; a port filter 536, and an optional port filter (not shown).

The bioreactor lid 534 provides for sterile needleless connectors 526 located at the ends of internal ports 538 and 540. The term "needleless connector" is understood to be a connector with no sharp needles (e.g. a blunt cannula). When the bioreactor lid 534 is assembled to the bioreactor base 530, internal port 538 is in fluid communion with the central tissue digestion chamber 532. Fluid may be transferred from port 538 to and from chamber 532 across an optional port filter (not shown). Similarly, internal port 540 within the bioreactor lid 534 is in fluid communion with the bioreactor base 530, which in turn is in fluid communion with the tissue digestion chamber 532. Fluid may be transferred from port 540 to the tissue digestion chamber across the port filter 536. The role of the port filters 536 is to retain tissue aggregates and biopsy debris within the tissue digestion chamber 532 while allowing the passage of disassociated cells out of the tissue digestion chamber 532, via port 540.

Loading of a tissue biopsy into the tissue digestion chamber 532 is performed with the bioreactor lid 534 removed from the bioreactor base 530. Following loading, the lid 534 and base 530 are assembled together and the tissue digestion chamber 532 is operationally engaged with the module 118 and then filled under automated control with an enzyme solution through port 540. The addition of enzyme solution to the tissue digestion chamber 532 is balanced by air escaping through air vent 542. Biopsy digestion takes place under continuous or intermittent recirculation of the enzyme solution, thereby keeping the released cells in suspension and maximizing the exposure of the biopsy to the enzyme reagents. During recirculation, the enzyme solution enters the bottom of the tissue digestion chamber 532 through the port filter 536 via port 540 and leaves the top of chamber 532 via port 538. This creates a fluid flow path in a direction opposite to the gravity vector such that the biopsy is suspended and tumbled to maximize the effectiveness of the enzyme reagents. Digestion may be enhanced by gentle agitation of the digestion medium within the digestion chamber via a mixing diaphragm (not shown). The air vent 542 may be closed during any recirculation steps, as any residual air bubbles present in the fluid flow system are trapped and retained in the upper half of the bioreactor, above the inlet of port 538. Upon completion of the digestion sequence, the application of reverse flow of either air or medium via port 538 into the top of the tissue digestion chamber 532 results in the dispensing of the disassociated cells past the port filter 536 and out of the bioreactor via port 540 to either a proliferation chamber assembly 600 or a cell collection vessel. It is understood by one of skill in the art that the tissue digestion bioreactor 500 can be optionally loaded with cells instead of a tissue, in this case digestion of the cells is not required.

Once the tissue digestion bioreactor 510 is assembled and placed within the outer protective containment unit 520, as shown in FIG. 5A, twin layers of containment and protection are present for transport from the operating room, where the biopsy is harvested, to the clinical area containing the system 100. Peel tape seals are present over the sterile needleless connectors 528 such that the sterility of these connectors is maintained until it is time to install this assembly 500 into the tissue engineering module 118.

Figure 6:
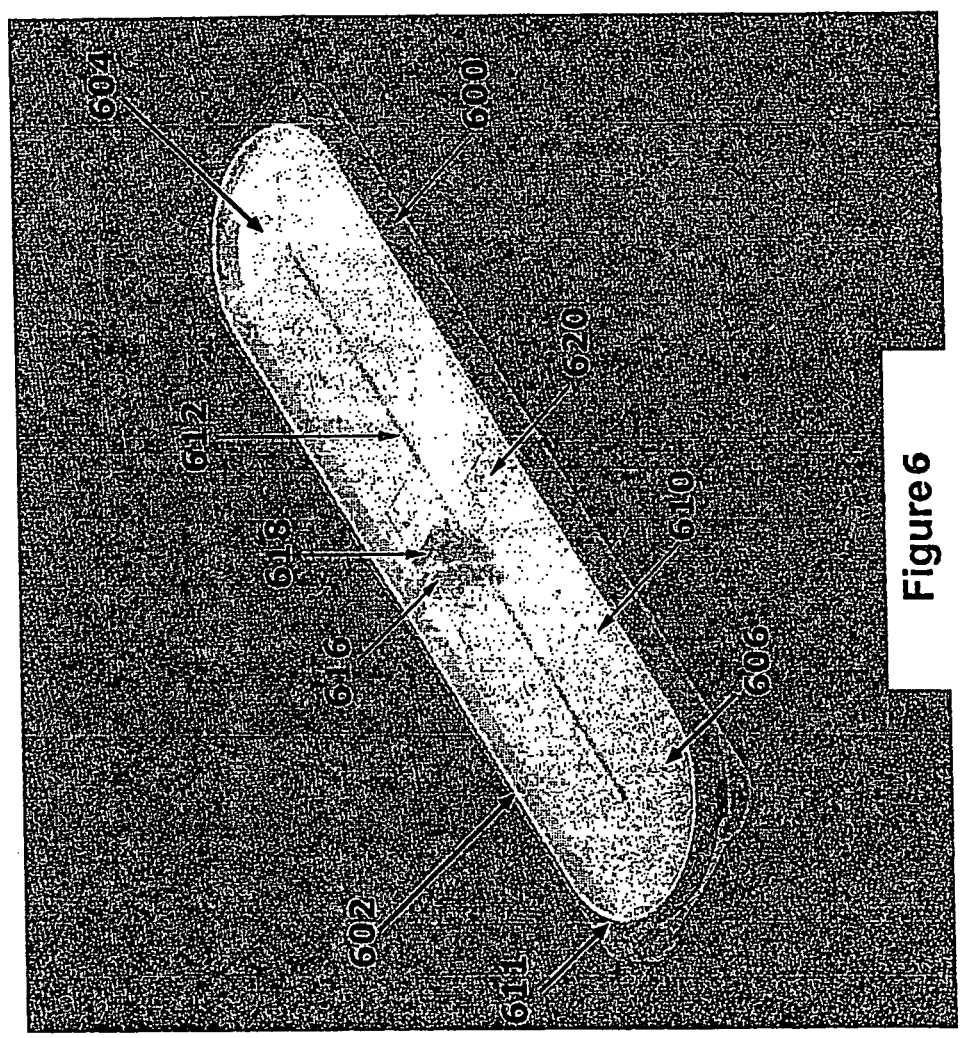
FIG. 6 shows a perspective view of an embodiment of a proliferation chamber assembly of the present invention.

FIG. 6 shows the proliferation chamber assembly 600. The proliferation chamber assembly 600 comprises a proliferation bioreactor 602 that has a proliferation chamber 604. The proliferation chamber 604 has a base 606 having a proliferation surface 610 suitable for cell attachment and growth and a lid 611 for containment of fluid. To adjust or maintain the levels of dissolved gases in the medium, a gas permeable membrane (not shown) may be incorporated to the top surface of the proliferation chamber 604 that allows the transport of gases such as oxygen and $CO_2$. Separation walls 612 divide the internal space of the proliferation chamber 604 into a channel system that forces medium to follow a predefined pathway from an inlet port 616 to an outlet port 618.

The design of the proliferation chamber assembly 600 has several important operational features. Relatively uniform cell seeding can be obtained by the infusion of a cell suspension through the channel system. Furthermore, the channel configuration ensures that media flow is well distributed over the whole proliferation surface 610, thereby reducing potential low-flow regions that may compromise local cell vitality due to reduced nutritional supply or waste product removal. Confluence sensors 620 may be distributed through the chamber 604 to automate the detection of final cell confluence. These sensors 620 provide feedback on the progress of the cell culture activity to facilitate automatic control over the entire process. In addition, information generated from the sensor data enables the operator to obtain advanced notification of processing status such that related clinical activities may be scheduled as appropriate.

At the conclusion of the proliferation sequence, continuous or intermittent recirculation of an appropriate enzyme solution through the channel system induces cell detachment due to the effect of the enzyme reaction and the low-level sheer stresses generated by the fluid flow. Accordingly, cell harvest is achieved without the need for mechanical shaking or rotation of the proliferation chamber assembly 600.

The channel system used herein can provide for a uniform distribution of cells to enable homogeneous cell feeding of the proliferation surface.

The inlet and outlet ports 616 and 618 connect with the proliferation chamber 604 via ducts (not shown) that increases in width as the base 606 of the proliferation chamber 604 is approached. This reduces the streamlining of the flow and allows a more uniform fluid distribution into and out of the proliferation chamber 604.

The interior height of the proliferation chamber 604 within the proliferation chamber assembly 600 has been optimized to obtain an intermediate height between a low height that allows air bubbles to bridge between the lid 611 and the proliferation surface 610 (causing cell necrosis), and a high height where the fill volume is excessive and air removal is problematic.

The proliferation bioreactor 602 optionally includes flow interrupters (not shown) that deliberately cause controlled turbulence along the length of the proliferation chamber 604. These interrupters are placed perpendicular to the flow as irregularities in the top surface of the proliferation chamber 604. The flow interrupters cause controlled mixing along the length of the chamber 604 so that free cells (particularly post release after confluence detection) remain in suspension and can be moved efficiently toward the outlet 618.

The proliferation bioreactor 602 optionally includes a progressive change in elevation along the length of the fluid pathway from inlet 616 to outlet 618 to enable the more complete exhaust of all contents. This elevation change is accomplished with both the proliferation surface 610 of the base 606 and the top surface of the chamber 604 changing in elevation at the same rate, thereby maintaining a consistent separation between the top surface and proliferation surface 610.

The proliferation bioreactor 602 optionally includes a vibratory element (not shown) that facilitates cell release from the proliferation surface 610. This element is optionally mounted directly onto the chamber 604.

The proliferation chamber 604 optionally includes multiple bases 606 (e.g. proliferation surfaces 610) in a stacked geometry whereby each level is either in series or in parallel in terms of fluid flow.

Figure 7B:
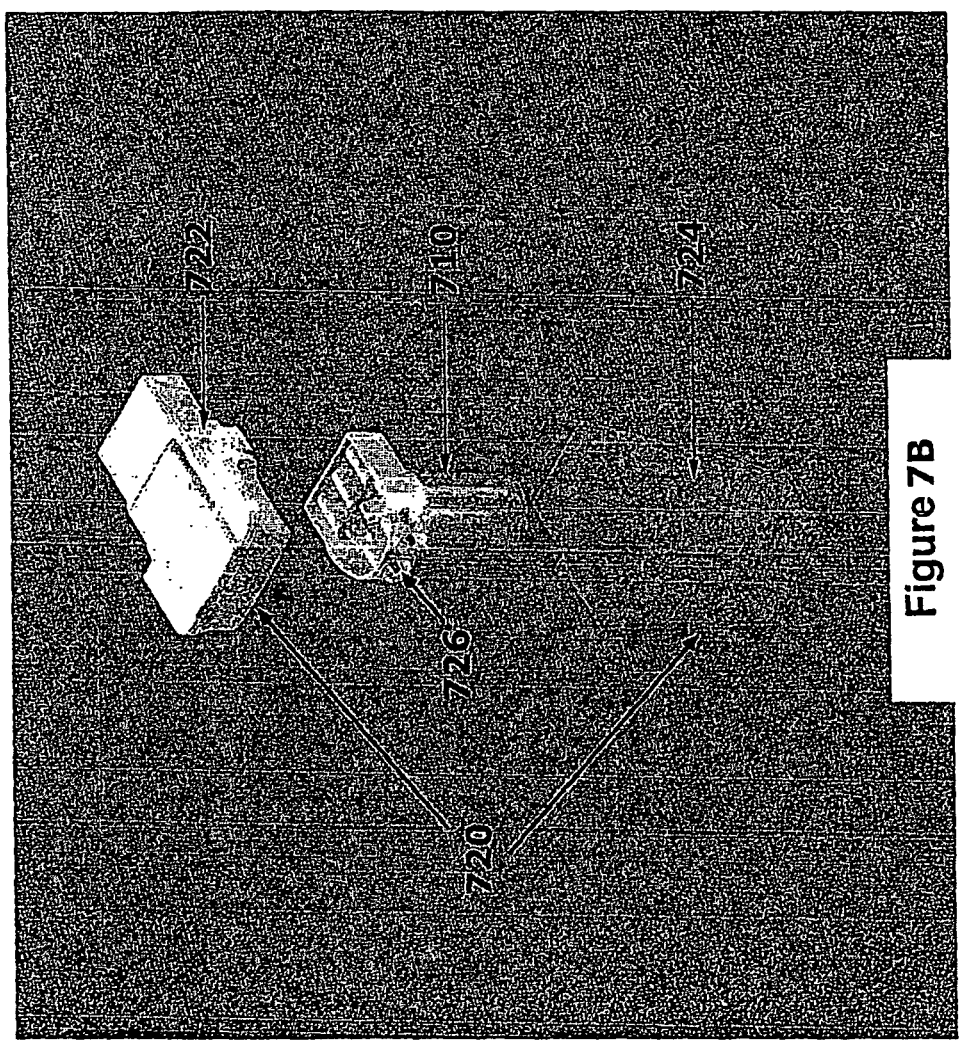
FIG. 7B shows a partial exploded view of the product chamber assembly of FIG. 7A showing a protective unit lid, a differentiation bioreactor, and a unit base.

FIG. 7A shows the product chamber assembly 700. FIGS. 7B and 7C illustrate the components of the product chamber assembly 700. The chamber assembly 700 comprises a differentiation bioreactor 710, described more fully with respect to FIG. 7C, and an outer protective containment unit 720. The outer protective containment unit 720 comprises a protective unit lid 722 and a unit base 724 to enhance the protection and isolation of the contents of the differentiation bioreactor 710 therein. The differentiation bioreactor 710 is connected to the protective unit lid 722 via sterile needleless connectors 726. Each of the connectors 726 is in direct fluid communion with a corresponding mating connector (not shown) of the protective unit lid 722. Once the differentiation bioreactor 710 is connected to the protective unit lid 722, the protective unit lid 722 is then connected to the unit base 724. This forms twin layers of containment and protection. Additionally, peel tape seals are present over the sterile needleless connectors such that the sterility of these connectors is maintained until it is time to install this assembly 700 into the tissue engineering module 118.

The differentiation bioreactor 710, designed to promote cell differentiation and subsequent tissue construct formation, is shown in FIG. 7C. The differentiation bioreactor 710 has four primary components: a bioreactor base 730 that substantially forms a differentiation/tissue formation chamber 732; a removable bioreactor lid 734; a permeable membrane tube 736; and a scaffold/membrane/matrix 738. The permeable membrane tube 736 tightly encircles the scaffold/membrane/matrix 738 to form a cell and tissue growth compartment 740 above the scaffold/membrane/matrix 738. The tissue growth compartment 740 may extend within the scaffold/membrane/matrix 738 according to the pore size of the scaffold/membrane/matrix 738 and the placement of the scaffold/membrane/matrix 738 within the membrane tube 736. The membrane tube 736 is also affixed to the inlet port 742, such that the membrane is physically located within the differentiation/tissue formation chamber 732. This divides the bioreactor into two independent compartments, a cell and tissue growth compartment 740 and an outer cell-free medium compartment 744, all within chamber 732. The pore size of the membrane tube 736 is selected on the basis of being impermeable for cells but permeable for nutrients, waste products, growth factors, etc., within the culture medium. If desired, membrane pore size can be chosen in a manner to exclude molecules of a certain molecular weight from passing through the membrane.

The inlet port 742 is required for loading a cell suspension into the tissue growth compartment 740 and for the perfusion of the emerging tissue construct with culture medium. During the delivery of the cell suspension into the empty tissue growth compartment, entrapped air within the tissue growth compartment 740 is allowed to exit through air vent 746. In a similar fashion, the outer cell free compartment 744 of chamber 732 is loaded with media via port 748 and entrapped air may escape via air vent 750.

The design of the differentiation bioreactor 710 allows direct perfusion of the tissue construct through media delivery to port 742 or indirect media supply to the surrounding cell free compartment 744 of chamber 732 via port 748. The indirect media supply is located away from that region of the implantable scaffold/membrane/matrix 738 that is seeded with cells so as to minimize the potential for damaging sheer stresses that could compromise the formation of cell aggregates. Typically, ports 746 and 750 are closed during perfusion and port 752 serves as a media outlet; however, various alternate media supply scenarios are possible based on specific tissue engineering requirements or advanced cell culture requirements. An important aspect of the media perfusion strategy is that the permeable membrane 736, which forms part of the tissue growth compartment 740, allows fresh culture medium to permeate into the tissue growth compartment 740 without any loss of cells away from the scaffold. Furthermore, nutrition is provided to the cells from essentially all directions without restrictions from any impermeable bioreactor walls.

The differentiation bioreactor 710 complete with the protective containment unit installed, as shown in FIG. 7A, represents the pre-assembled and sterilized format for the assembly 700. In use, this assembly 700 is removed from the tissue engineering module 118 upon completion of the biological processing and is transferred to the operating room. By virtue of the progressive layers of containment, the assembly is ideally suited for operating room aseptic procedures.

FIGS. 8A to 8C show the configuration of another embodiment of a product chamber assembly of the present invention. FIG. 8A shows a product chamber assembly 800. FIGS. 8B and 8C illustrate the components of the product chamber assembly 800. The chamber assembly 800 comprises a cell therapy bioreactor 810, described more fully with respect to FIG. 8C, and an outer protective containment unit 820. The outer protective containment unit 820 comprises a protective unit lid 822 and a unit base 824 to enhance the protection and isolation of the contents of the cell therapy bioreactor 810 therein. The cell therapy bioreactor 810 is connected to the protective unit lid 822 via sterile needleless connectors 826. Each of the connectors 826 is in direct fluid communion with a corresponding mating connector (not shown) of the protective unit lid 822. Once the cell therapy bioreactor 810 is connected to the protective unit lid 822, the protective unit lid 822 is then connected to the unit base 824. This forms twin layers of containment and protection. Additionally, peel tape seals are present over the sterile needleless connectors such that the sterility of these connectors is maintained until it is time to install this assembly 800 into the tissue engineering module 118.

The cell therapy bioreactor 810 receives cells following proliferation and cell washing. The bioreactor 810 is shown in FIG. 8C. The cell therapy bioreactor 810 has a bioreactor lid 828 connected to a vertical chamber 830 and a bioreactor base 832 that contains a conical cell collector 834. When the lid 828 is connected to the bioreactor base 832 for operation in the module 118, a cell suspension may be introduced into the bioreactor 810 and under quiescent conditions the cells settle by gravity into the conical cell collector 834. The combination of a sealed bioreactor chamber shelf 836 and the fluid return tube 838 allows the remaining fluid above the conical cell collector 834 to be removed from the bioreactor 810 thus leaving concentrated cells within the conical cell collector 834 ready for implantation.

The cell therapy bioreactor 810 complete with the protective containment unit installed, as shown in FIG. 8A, represents the pre-assembled and sterilized format for the assembly 800. In use, this assembly 800 is removed from the tissue engineering module 118 upon completion of the biological processing and is transferred to the operating room. By virtue of the progressive layers of containment, the assembly is ideally suited for operating room aseptic procedures.

Figure 9:
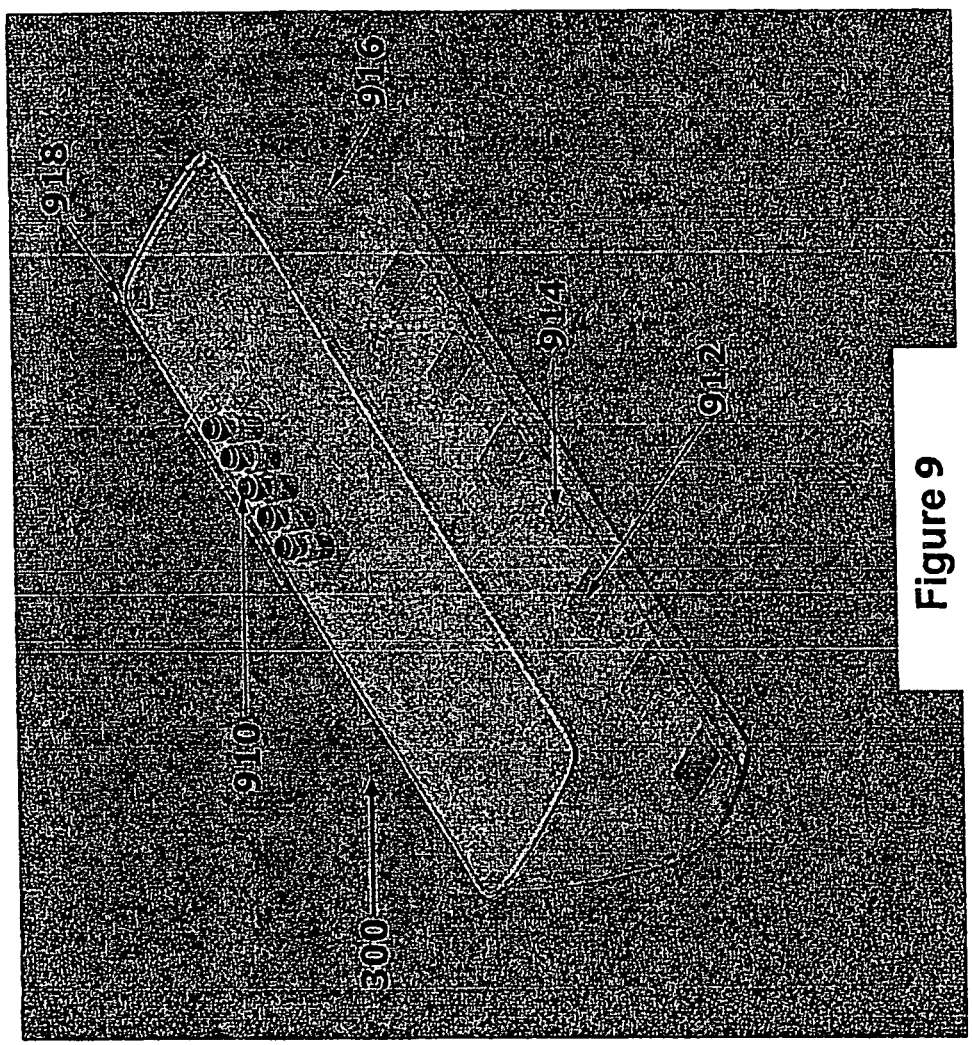
FIG. 9 shows a perspective view of an embodiment of a fluid reservoir of the present invention.

FIG. 9 shows the fluid reservoir 300. The internal elements of the fluid reservoir 300 are a set of flexible bags (not shown) used to contain all of the processing fluids and waste fluids. These bags are connected to the fluid pathway (not shown) via the needleless connections 910. Prior to connection of the fluid reservoir 300 to the upper housing 200 of the tissue engineering module 118, connections 910 are also used to install fluids into each bag, as well as provide access for adding final components (such as autologous serum). In order to ensure that the fluids contained within the bags in the fluid reservoir 300 remain viable for the extended periods required for cell culture and tissue engineering, the fluid reservoir 300 has been designed to allow for reduced temperature operation as compared with the remainder of the tissue engineering module 118, which typically operates at 37° C. The reduced temperature within the fluid reservoir 300 is attained via a temperature controller, such as Peltier™ cooling elements on the base of the system bay (not shown), which protrude upwardly into the fluid reservoir 300 through holes 912 to provide local cooling to the bags. The bag temperature sensor (not shown) resides on the base of the system bay (not shown) and protrudes through a hole 914 in the fluid reservoir 300 to provide the control feedback necessary for temperature control. Local cooling within the overall module 118 for the tissue engineering system 100 has the advantage of minimizing the power required for cooling and also minimizing problems associated with condensation. To ensure that there is adequate insulation for the inner fluid reservoir bags, the fluid reservoir 300 is constructed to be a double walled reservoir 916. An air space is present between the two walls thereby improving the insulation properties of the reservoir 300 while, preferably, maintaining optical clarity for inspection. Through active cooling of the fluid reservoir 300, the contents remain in a refrigerated state thereby minimizing or eliminating operator intervention to replace fluids that would otherwise expire if maintained continuously at 37° C. Latches 918 on the corners of the fluid reservoir 300 provide the connection points that assemble the fluid reservoir 300 to the upper housing 200 of the tissue engineering module 118.

Figure 10:
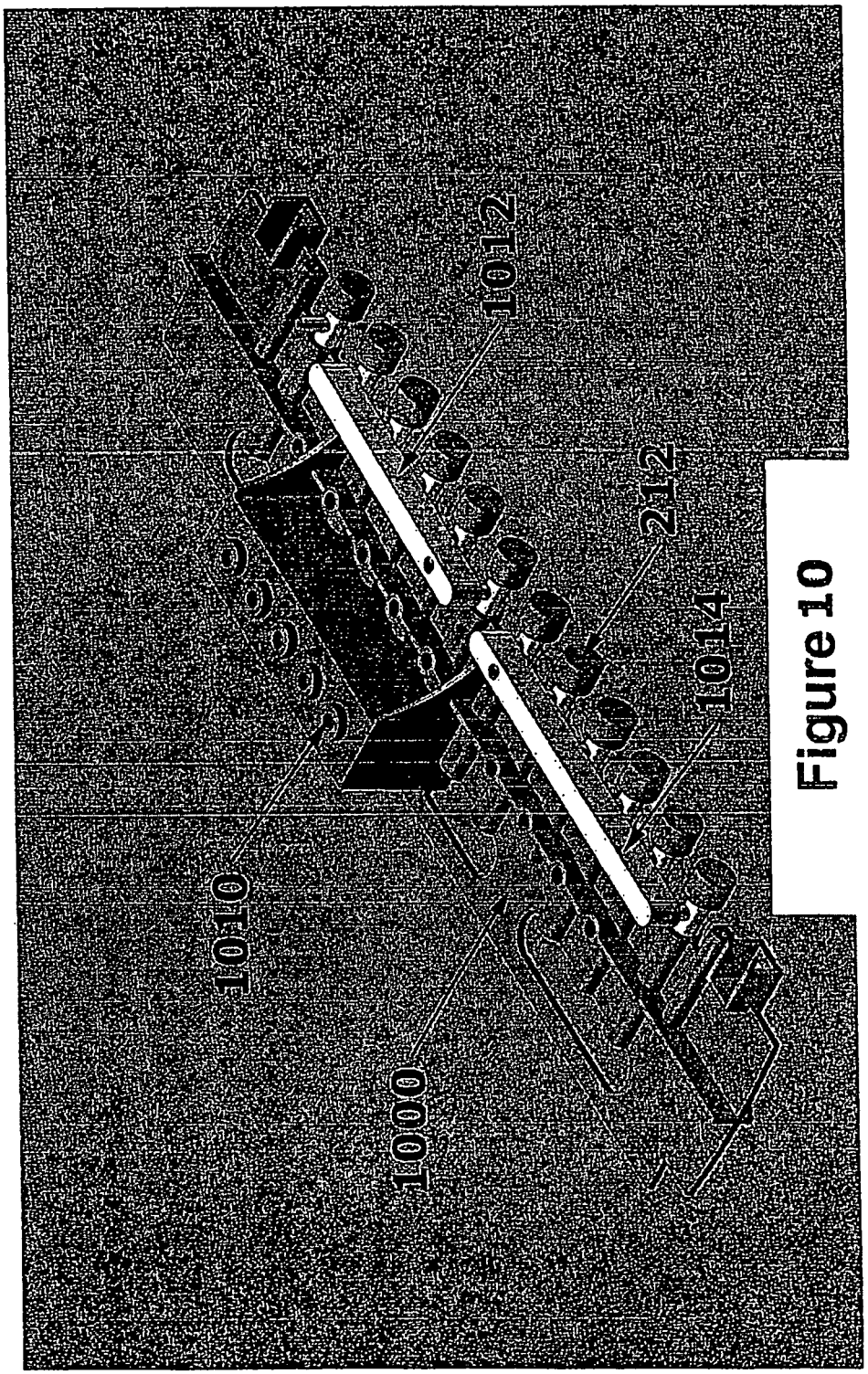
FIG. 10 shows a perspective view of an embodiment of a flow control valve housing of the tissue engineering module of FIG. 3.

FIG. 10 shows a flow control valve housing 1000 of the upper housing 200, which is used as the main fluid pathway tube interconnect and fluid direction interface between the chamber assemblies 500, 600 and 700 and the fluid reservoir 300. The flow control valve housing 1000 is constructed as a molded plasic component that makes connections to the fluid reservoir 300 through the series of cannula connections 1010. Fluid control is obtained via flow control valves 212 that are installed into the flow control valve housing 1000. The flow control valve headers 1012 and 1014 provide a common fluid connection between the flow control valves 212 and enables the internal fluid pathway connections between the chamber assemblies 500, 600 and 700 and the fluid reservoir 300. This housing 1000 and related vertical plates (not shown) dramatically simplifies the internal tubing complexity for the fluid management system used within the tissue engineering module 118.

Figure 11:
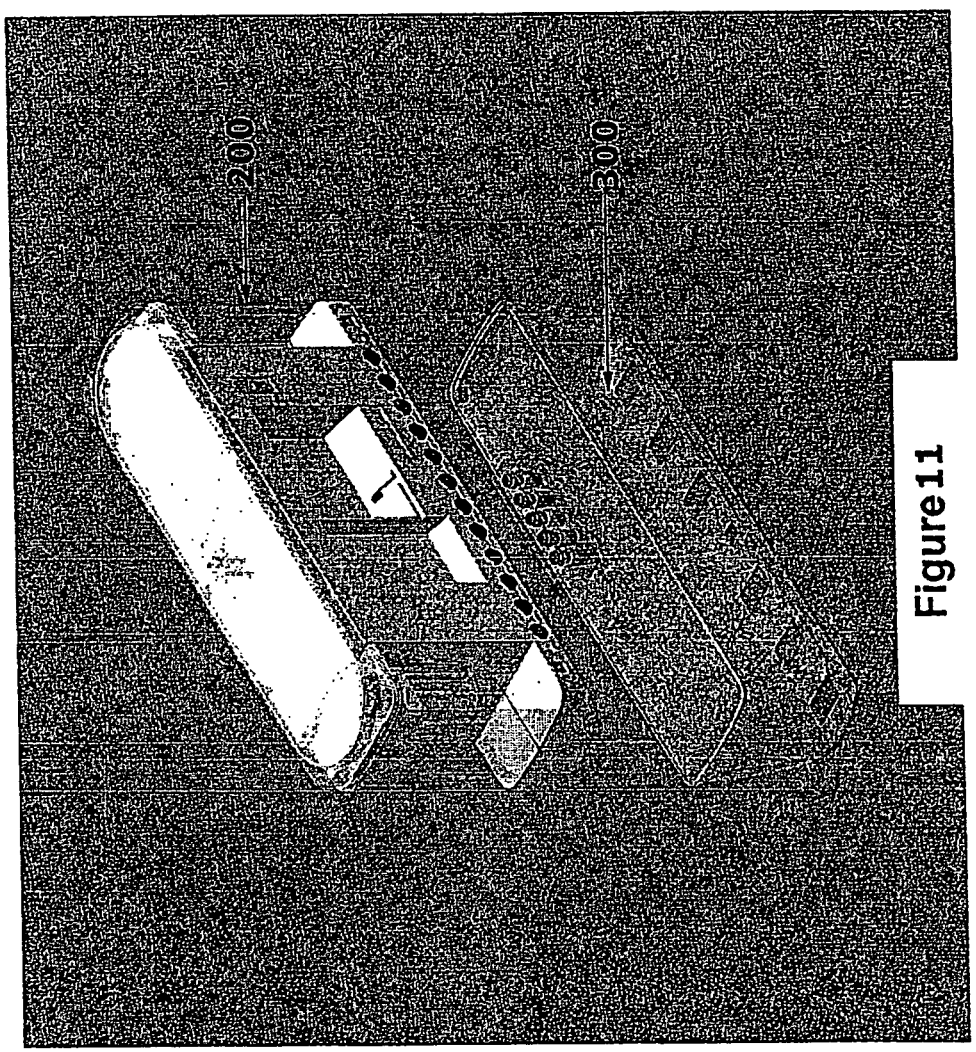
FIG. 11 shows an exploded view of the tissue engineering module of FIG. 4 with the fluid reservoir of FIG. 9.

FIG. 11 shows an exploded view of the tissue engineering module 118 of FIG. 4 with the fluid reservoir 300 of FIG. 9. FIG. 11 shows the two main components of the tissue engineering module 118 in the final stage of installation; the upper housing 200 and the lower fluid reservoir 300. To summarize, the upper housing 200 contains the installed tissue digest bioreactor 510 within a protective containment unit 520; the proliferation chamber assembly 600; the installed differentiation bioreactor 710 within the protective containment unit 720 or the cell therapy bioreactor 810 within the protective containment unit 820; and the flow control valve housing 1000. The tissue engineering module 118 contains internal crossflow cell concentrator (not shown) and interconnect tubing and valves to complete the fluid handling system (not shown). Connection of the upper housing 200 to the fluid reservoir 300 automatically engages a series of fluid connectors that enable fluid communication between the two components 200 and 300. Both components 200 and 300 are held together by molded latches (not shown) on the upper housing 200 and molded latches 918 on the fluid reservoir 300.

Figure 12:
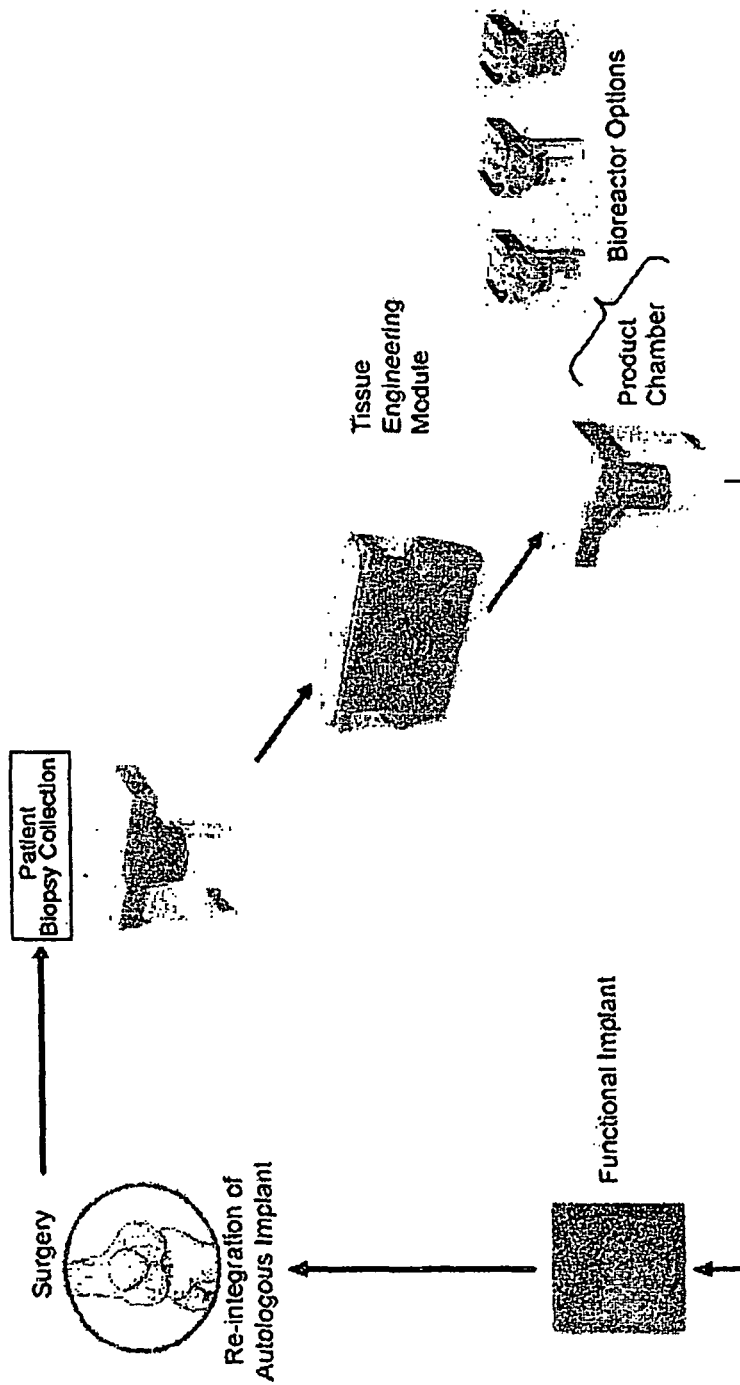
FIG. 12 shows a scheme of a general methodology for clinical tissue engineering using the tissue engineering module of FIG. 3.

FIG. 12 shows a scheme of a general methodology for clinical cell therapy and tissue engineering using the tissue engineering module 118 of FIG. 3, operating in the tissue engineering system 100 of FIGS. 1 and 2, and autologous cartilage tissue engineering as a representative example. In such an example, cells (i. e. chondrocytes) are obtained from a surgical biopsy of a patient and placed in the tissue digestion bioreactor 510 of the tissue digestion chamber assembly 500. The tissue digestion chamber assembly 500 is engaged with the tissue engineering module 118 containing the proliferation chamber assembly 600 and product chamber assembly 700. A central microprocessor is present within the tissue engineering system and controls and customizes the internal environment of the bioreactor/chambers, and hence facilitates tissue growth therein, resulting in the stimulation of cell growth and subsequent matrix expression to generate an implant. Sensors within the bioreactor provide feedback to the microprocessor to ensure that the cells are seeded, expanded and differentiated in a desired and controlled manner to provide an autologous tissue implant. Once the implant is generated, the product chamber assembly 700 is removed from the module 118 and transported to the operating room for surgical implantation into the patient. The present system provides an advantageous way to provide autologous tissue engineered implants in a sterile, safe, convenient and efficacious manner. Furthermore, the ability to prepare tissue engineered implants in a clinical setting allows considerable flexibility in the locations for undertaking the tissue engineering process. While the system can be used in a centralized location, the design and automated operation of the system enables clinical use at regional centers. Such widespread availability precludes the transportation of biological material to and from centralized cell/tissue processing facilities, thereby improving the cost effectiveness and efficiency of the tissue engineering process while avoiding shipment, tracking and regulatory complications.

Figure 13:
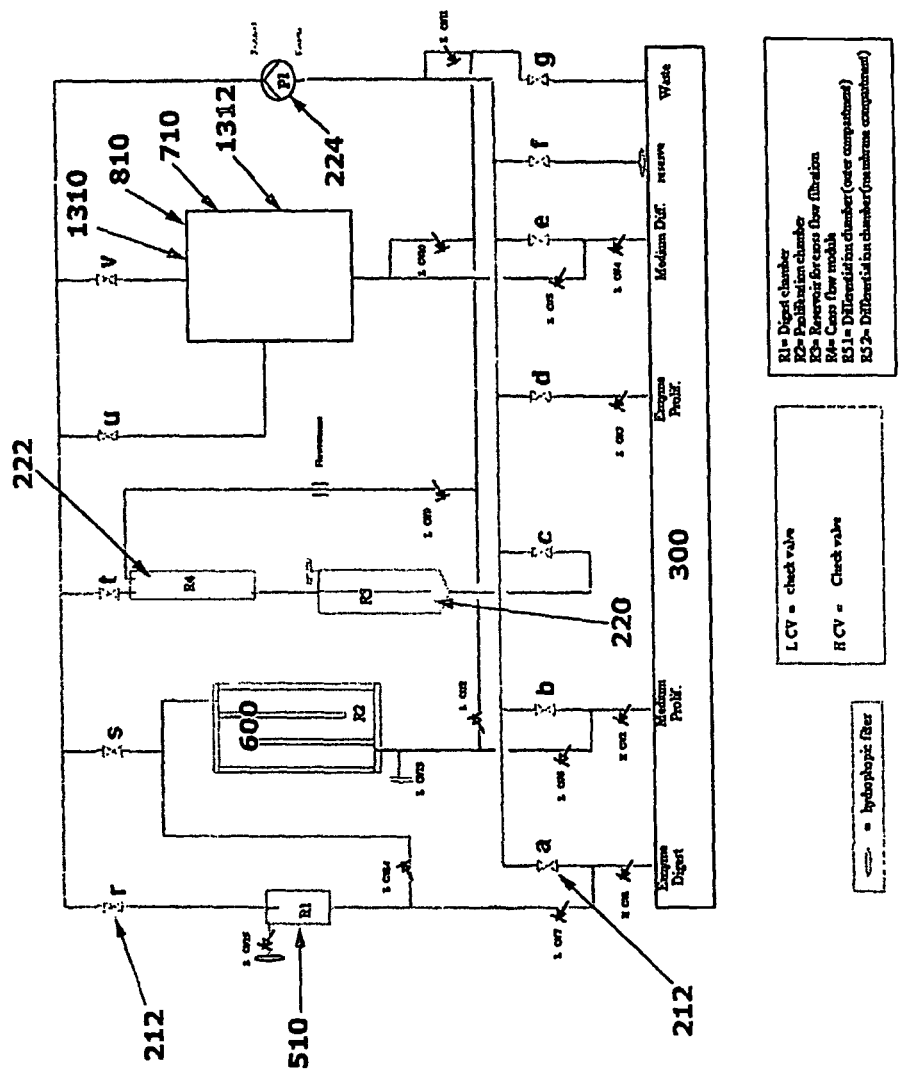
FIG. 13 shows an embodiment of a fluid flow schematic.

FIG. 13 illustrates an embodiment of a fluid flow schematic in which the bioreactors/chambers of FIGS. 5 and 6, and either 7 or 8 may be employed. A tissue digestion bioreactor 510 is present that accommodates a tissue biopsy. A proliferation chamber assembly 600 is present that is configured to accept cells from the tissue digestion bioreactor 510 and allows seeding of the proliferation surface 610. Bubble traps within the tissue digestion bioreactor 510 remove air bubbles from the input line to the proliferation chamber assembly 600 and therefore prevents these bubbles from entering the proliferation chamber assembly 600 and potentially compromising localized cell populations. A cell washing reservoir 220 is present to accept the expanded cell numbers from the proliferation chamber assembly 600 and to serve as a temporary holding container during a cell washing and cell concentration procedure performed with the aid of a cross flow filtration module 222. One of several alternative product bioreactors (e.g. cell therapy bioreactor 810, differentiation/tissue formation bioreactor 710, a multi-implant bioreactor 1310, or a cell matrix implant bioreactor 1312) is also present and is configured to accept the cells from reservoir 220 after the washing and concentration step.

Tissue engineering reagents (i.e. media, enzyme solutions, washing solutions, etc.) and waste fluids are stored in a fluid reservoir 300 such as that shown in FIG. 9. Fluid flow through the system is directed by the operation of a fluid pump 224, flow control valves 212a-212g and 212r-212v according to control inputs from a central microprocessor. Air filters allow the transfer of air into or out of the system as required during operation without compromising system sterility. Furthermore, in-line gas exchange membranes (not shown) may be deployed at various locations within the fluid flow paths to facilitate the control of dissolved gases in the culture medium.

In one non-limiting example of the system operation, a tissue biopsy is inserted into the tissue digestion bioreactor 510 of the tissue digestion chamber assembly 500. A digestion medium containing enzymes is pumped into the tissue digestion bioreactor 510 from the fluid reservoir 300 to initiate the digestion process. The digestion medium may be continuously or periodically re-circulated via pump 224, thereby keeping the released cells in suspension and maximizing reagent exposure to the biopsy. Introduction of a proliferation culture medium from the fluid reservoir into the top of the tissue digestion bioreactor 510 transfers the cell suspension to the proliferation chamber assembly 600 and simultaneously dilutes the enzyme solution to a concentration that is tolerable for cell proliferation. The transfer of partially digested tissue out of the digestion bioreactor 510 is precluded by port filter that is sized to allow passage of disassociated cells and retention of cell aggregates. Cells generated from the biopsy digestion process are homogeneously distributed throughout the proliferation chamber assembly 600 either by the recirculation of the cell suspension via the activation of valves 212 and the pump 124, or by the automated application of gentle shaking of the proliferation chamber assembly 600.

Following a quiescent period to allow attachment of the cells to the proliferation surface 610, the proliferation medium is periodically or continuously replaced with fresh proliferation medium from the fluid reservoir 300. During a medium replacement step, the supply of fresh medium from the fluid reservoir 300 is balanced by the discharge of waste fluid to a waste container in the fluid reservoir 300 via valve 212g.

Once the cell culture approaches confluence, the media within the proliferation chamber assembly 600 is evacuated into the waste container within the fluid reservoir. In this process, the removal of fluid from the proliferation chamber assembly 600 is balanced by incoming sterile air delivered via an air filter or by incoming PBS wash solution from the fluid reservoir 300.

The cells are subsequently released from the proliferation surface 610 through an automated sequence, such as the delivery of enzymes (for example trypsin) and the timed recirculation of the cell suspension or the timed application of impact or agitation to the bioreactor via an impact drive. In order to remove the enzymes and to collect the cells in a relatively small volume of medium for subsequent transfer to a selected product bioreactor (710, 810, 1310, or 1312) of the product chamber assembly, the cell suspension is transferred from the proliferation chamber assembly 600 to the cell washing reservoir 220. The cell suspension is then continuously recirculated via valves 212 and pump 224 through the cross-flow filtration module 222. The membrane in the cross-flow filtration module 222 prevents the loss of cells but allows a certain percentage of media (permeate) to be removed via valve 212g to the waste container in the fluid reservoir 300. The result is a reduction of the suspension volume and/or dilution of any enzymes present, provided the removal of permeate is compensated by the supply of fresh medium from the fluid reservoir 300. The continuous flow reduces the potential for cells to become entrapped within the membrane of the cross-flow filtration module 222.

Cell delivery to the product bioreactor is achieved by transferring the washed cells from the reservoir 220 via the valves 212 and pump 224. Following cell transfer to the product bioreactor, fresh media may be introduced into the product bioreactor through the operation of pump 224. During biological processing, the medium is periodically or continuously replaced with fresh medium from the fluid reservoir 300. During a medium replacement step, the supply of fresh medium from the fluid reservoir 300 is balanced by the discharge of waste fluid to a waste container in the fluid reservoir via valve 212g. In between the medium replacement steps, the fluid within the product bioreactor is continuously or periodically recirculated under the control of pump 224 and valves 212. In order to ensure that environmental conditions within the different bioreactors promote normal cellular activity, conditions are monitored and controlled for the period necessary for the successful collection of expanded cells in the case of cell therapy or formation of one or more tissue constructs in the case of tissue engineering. Once the collection of cells or formation of tissue implants is complete, the product bioreactor is removed and transported to the operating room for subsequent clinical use It should be noted that the system/module of the invention is not limited to a particular type of cell or tissue. For example, a skeletal implant may be prepared for use in the reconstruction of bone defects. In this application, bone marrow could be used as the source of the primary and/or precursor cells required for the tissue engineering process. Accordingly, there is no requirement to perform tissue digestion; hence, the bioreactor chamber assembly may be of the type that only supports proliferation and differentiation. Depending on the available cell population and the required size of the implant, even proliferation may not be required. In this case, the configuration of the bioreactor chamber assembly may be directed to the single stage of cell differentiation and ongoing tissue formation. The final tissue construct could be comprised of an implantable scaffold, which may be composed of a bone biomaterial such as Skelite™, with active bone cells lining the open pores of the scaffold and actively laying down new mineralized matrix (osteoid). Such an implant would be quickly integrated at the implant site thereby accelerating the recovery process.

When two or more chamber assemblies are used in the module, the chamber assemblies may be independently operable or co-operatively operable. For example, the chamber assemblies may be operatively connected such that there is an exchange of fluids, cells and/or tissues from chamber to chamber or the chamber assemblies may operate independent of one another. The chamber assemblies may be connected via at least one of a passageway, tubing, connector, valve, pump, filter, fluid access port, in-line gas exchange membrane, and in-line sensor.

The tissue engineering system of the present invention is designed to perform activities under aseptic operating conditions. The system is fully automated, portable, multifunctional in operation and performs/provides without being limited thereto, one or more of the following:

sterile reception/storage of tissue biopsy;
automated monitoring of digestion process
digestion of biopsy tissue to yield disassociated cells;
cell sorting and selection, including safe waste collection;
cell seeding on or within a proliferation substrate or scaffold
proliferation of cells to expand cell populations;
cell washing and cell collection;
cell seeding on or within a tissue engineering scaffold, membrane and/or matrix;
cell differentiation to allow specialization of cellular activity;

tissue formation;
mechanical and/or biochemical stimulation to promote tissue maturity;
harvesting the tissue engineered constructs/implants for reconstructive surgery; and
storage and transportation of implantable tissue.

The tissue engineering system of the present invention may be pre-programmed to perform each of the above noted steps and/or other steps, individually, sequentially or in certain predetermined sequences or partial sequences as desired and required. Furthermore, each of these steps, or any combination thereof, are accomplished within one or more chamber assemblies on a tissue engineering module. In operation, the tissue engineering system is pre-programmed and automatically controlled thus requiring minimal user intervention and, as a result, enhances the efficiency and reproducibility of the cell culture and/or tissue engineering process while minimizing the risks of contamination. Therefore, in one example, the automated tissue engineering system of the present invention is capable of multi-functionally carrying out all of the steps of a biopsy tissue digestion to yield disassociated cells, subsequent cell seeding on a proliferation substrate, cell number expansion, controlled differentiation, tissue formation and/or production of a tissue implant within a single system.

The tissue engineering system and tissue engineering module is not to be limited to tissue engineering per se. The system and module can be utilized, for example, for cell therapy. Therefore, the applicability of the system and module of the present invention ranges from tissue engineering; to the formation of cells and/or tissues on and/or within at least one scaffold, membrane and matrix; to, simply, the expansion of cells for cell therapy applications. It is noted that the scaffolds/membranes/matrices can be any suitable shape, such as contoured, circular, have an irregular perimeter. The term "cell matrix implant" used herein is understood to encompass cells within and/or on a scaffold, matrix, and/or membrane, such as, and without being limited thereto, a pre-tissue.

Cells and tissues may be selected from, and without being limited thereto, non-cartilage tissue, such as cardiac tissue, vascular implants, and skin grafts, and skeletal tissues such as bone, cartilage, tendon, disc, related bone and cartilage precursor cells, and combinations thereof. More specifically, cells suitable for use in chamber assemblies, module and system of the invention are selected from but not limited to the group consisting of embryonic stem cells, adult stem cells, osteoblastic cells, pre-osteoblastic cells, chondrocytes, nucleus pulposus cells, pre-chondrocytes, skeletal progenitor cells derived from bone, bone marrow or blood, including stem cells, and combinations thereof. The cells or tissues may be of an autologous, allogenic, or xenogenic origin relative to the recipient of an implant formed by the cell culture and tissue engineering functions of the invention. It is also understood that the term tissues, as used herein, is not to be limited only to connective tissues but can include a variety of tissues such as, and without being limited thereto, cardiac tissue, vascular implants, and skin grafts.

The chamber assemblies of the present invention may provide an environment for at least one of the following selected from the group consisting of storage of tissue biopsy, digestion of tissue biopsy, cell sorting, cell washing, cell concentrating, cell seeding, cell proliferation, cell differentiation, cell storage, cell transport, tissue formation, implant formation, storage of implantable tissue and transport of implantable tissue.

The sensors used herein, such as, for example, confluence sensors, may have ability to monitor the specific performance of cell populations/tissue in said at least one chamber assembly from various donors and thereby, allow the system to accommodate for the requirements of cells/tissue of individual donors in said at least one chamber assembly. For example, as a result of these sensors, the system has the ability to adapt to the needs of specific cells/tissues from different donors. For instance, cells from an older donor may grow at a slower rate compared to a younger donor, therefore, the sensors would permit the system to adjust accordingly to permit longer growth times.

In addition, the tissue engineering module of the present invention can have at least one additional chamber assembly that can share a common process with an existing chamber assembly such that the additional chamber assembly can be removed in order to provide analysis and/or evaluation of the contents of the chamber that parallels the contents of the existing chamber. The contents may be media, tissue and/or cells.

The advanced tissue engineering system of the present invention has several advantages compared to methods and systems of the prior art. In particular, the turn-key operation of the device enables complex tissue engineering procedures to be performed under automated control in the clinic, thereby precluding the need to transport cells to centralized facilities for biological processing. The system is simple to use and obviates the existing time consuming and expensive manual human tissue culture procedures which can lead to implant contamination and failure. The tissue engineering modules and associated subsystem assemblies may be customized for the type of cell or tissue to be cultured and may be fabricated from any suitable biocompatible and sterilization tolerant material. The entire tissue engineering module or specific components thereof are replaceable and may be considered disposable. The tissue engineering module may be provided in a single-use sterile package that simplifies system set-up and operation in clinical settings. In other embodiments, any components such as the tissue digestion chamber assembly and product chamber assembly as well as the housing and the fluid reservoir can be provided separately packaged for use as a kit. In embodiments of the invention, the tissue digestion chamber assembly and the product chamber assembly with a selected bioreactor therein, may be provided separately packaged and as such can be provided as a kit to be used with a tissue engineering module. The proliferation chamber assembly in aspects is fabricated already attached to the housing of the tissue engineering module. All detachable aspects of the tissue engineering module are designed to ensure that assembly can only be done with the correct orientation and once assembled is essentially tamperproof.

It is understood by those skilled in the art that the tissue engineering module and device of the present invention can be fabricated in various sizes, shapes and orientation. The device can be fabricated to incorporate a single tissue engineering module or multiple modules in vertical or horizontal formats. Accordingly, the subassemblies can be made to correspond to the spatial format selected for the tissue engineering device. As such, different types of tissue engineering can be simultaneously conducted in a single device with each tissue engineering sequence being automatically monitored and controlled on an individual basis. It is also within the scope of the invention to have a plurality of automated tissue engineering systems operating and networked under the control of a remote computer.

The present invention is an improvement to the Applicant's automated tissue engineering system described in International Patent Application No. WO 03/0872292. The improvements to the advanced tissue engineering system of the present invention are generally discussed below.

In one aspect of the invention, the tissue engineering module still contains multiple bioreactors provided within chamber assemblies to allow multistage processing (digest/proliferation/differentiation); however, there are new aspects to the tissue engineering module as follows:

- The flow pathway of the advanced system is comprehensively revised reducing the number of valves. This can be achieved through an innovative use of check valves with specific cracking pressures;
- Since the advanced system can be comprised of a series of disposable components assembled in the clinic at the time of use (disposable tissue engineering module, fluid reservoir, chamber assemblies (tissue digestion, proliferation and one of four or more product chambers)), the tissue engineering module can include assembly integrity sensors that monitor that all parts are present and are connected together correctly;
- Predictive software can be included in combination with biosensor feedback to enhance control over the bioprocessing of the advanced system enabling the implantation surgery to be forecast in advance;
- The advanced system can accommodate the use of autologous (patient) serum as well as autologous cells, thereby minimizing risk;
- The advanced system can allow for multiple sample ports for the removal of media and/or cell and media samples;
- In addition, in the advanced system, ports can be available to allow mid process loading of additional media and/or additives, in the event this is necessary for certain clinical activities; and
- In addition to the assessment of cell vitality and cell number as part of a quality control kit, the advanced tissue engineering system can support the innovative use of assays in the form of microarrays and protein expression arrays. This is facilitated by the fact that a user may have access to the various components of the module such as for example the proliferation chamber assembly. In this manner, cells may be tested for expression of certain genes and proteins at various steps during the processing and operation of the system.

The Reservoir

- The fluid reservoir is installed as a separate unit (as shown in FIG. 11) and, in one embodiment, fluid connections are provided via connectors, such as an array of needleless ports, on the top surface that engages with mating connectors present in the upper housing of the tissue engineering module. The connectors and mating connectors are in fluid communication with one another;
- The fluid reservoir is optionally pre-filled;
- The fluid reservoir is optionally pre-sterilized;
- The fluid reservoir may be structurally rigid for ease of handling;
- The attachment of the fluid reservoir to the tissue engineering module may be via a one-way snap-on connection. Once attached, the reservoir cannot be detached; thereby, precluding potentially hazardous (and contra-indicated) re-use;
- The fluid reservoir may be clear for inspection of contents and to allow visible confirmation of additive loading prior to connection to the cassette;
- The fluid reservoir may have open "windows" in the base to enable thermal union with Peltier (or similar) cooling members that emerge from the base of the bay present on the instrument;
- The fluid reservoir may be designed with twin walls to maximize the insulation properties when operated at 4° C. and the remainder of the instrument at 37° C.

The Bioreactors

The bioreactor design is significantly different than the Applicant's earlier PCT application. While the basic internal working of the tissue digestion bioreactor, the proliferation bioreactor, and the differentiation bioreactor for implant formation are per the Applicant's earlier International Patent Application No. WO 03/0872292, the design has been improved. In one particular embodiment, a novel design for the provision of a double containment for selected bioreactors has been implemented to improve and maintain aseptic conditions during transport of these bioreactors to or from the clinic or operating room. The chamber assembly for the tissue digestion bioreactor and/or the product bioreactor (differentiation bioreactor) comprises an outer protective unit that houses the selected bioreactor therein. The outer protective unit comprises a unit lid and unit base. Engaged within the outer protective unit is a desired bioreactor that comprises a bioreactor lid and bioreactor base. The bioreactor lid may be supported and engageable with a portion of the unit lid by needleless injectors.

Chamber Assembly—with Tissue Digestion Bioreactor

- The chamber assembly having a tissue digestion bioreactor therein is designed to accept a tissue biopsy (for example but not limited to a cartilage biopsy, in other aspects may be loaded with cells) and facilitates directed flow as outlined in the Applicant's International Patent Application No. WO 03/0872292. In one embodiment, the tissue digestion bioreactor within the assembly is formed with the bioreactor base chamber containing an integral lower tubing connection such that all the flow port connections occur at the top. This enables connection to a top manifold through sterile needleless connections (FIGS. 5B and 5C).
- In addition the tissue digestion bioreactor chamber assembly may be produced with two "containment layers" whereby the tissue digestion bioreactor and connection ports are loaded into an outer protective containment unit with a further set of connection ports (FIGS. 5B and 5C). The ports are designed to allow aseptic docking once the protective port covers (tabs or adhesive labels) are removed. This twin level of protection provides important added security to prevent inadvertent contamination as the tissue digestion bioreactor within the chamber assembly is being transported from the site of biopsy collection (e.g. operating room) to the location of the advanced tissue engineering system (e.g. clinical lab).

Chamber Assembly—with a Proliferation Bioreactor

The proliferation bioreactor is similar to the "s-channel" bioreactor shown in Applicant's International Patent Application No. WO 03/0872292. However, there are several changes made thereto that provide important improvements:

- One embodiment of the layout of the proliferation bioreactor is in a race-track configuration (FIG. 6) that is similar but not limited to the letter "C". This allows the inlet and outlet to be placed at the center of the tissue engineering module, thereby facilitating tubing connections.
- The race-track has inlet and outlet ports that enter the proliferation chamber with a duct that increases in width as the chamber is approached. This reduces the streamlining of the flow and allows a more uniform fluid distribution into and out of the chamber.

The volume of the proliferation bioreactor was considered in terms of the resulting dilution that occurs when the incoming cell suspension released from the digest bioreactor is mixed with incoming media to fill the proliferation chamber. It was found that residual enzymes initially used in the digestion process do not need to be physically removed or deactivated (to preclude cell complications during proliferation) when dilutions of for example about 10:1 occurs during the loading of the proliferation chamber.

The height of the proliferation bioreactor can be optimized to obtain an intermediate height between a low height that allows air bubbles to bridge between the top surface and the active cell surface (causing cell necrosis), and a higher height where the fill volume is excessive and air removal is problematic.

The proliferation bioreactor can optionally include flow interrupters that deliberately cause controlled turbulence along the length of the proliferation surface. These interrupters would be placed perpendicular to the flow as irregularities in the ceiling of the proliferation chamber. The objective is to cause controlled mixing along the length of the proliferation surface so that free cells (particularly post release after confluence detection) remain in suspension and can be moved efficiently toward the outlet.

The proliferation bioreactor may optionally include a slight elevation change from inlet to outlet (cork-screw style or similar to a spiral ramp) to enable the more complete exhaust of all contents. This elevation change would be accomplished with both the floor and ceiling of the cavity decreasing in elevation at the same rate, thereby maintaining a consistent interior height.

The proliferation bioreactor includes sensors to monitor the onset of cell confluence. In one aspect, sensor electrodes reside on the proliferation surface and are exposed to the media to monitor the changes in impedance that occurs with increasing cell growth.

The proliferation bioreactor optionally includes a vibratory element that facilitates cell release from the proliferative surface of the chamber. This element is mounted directly in the chamber.

In addition, multiple proliferation bioreactors may be incorporated.

Chamber Assembly—with Product (i.e. Implant) Bioreactor

Four different product bioreactors may be selected for use in the product chamber assembly (identified generically as differentiation bioreactors in the Applicant's International Patent Application No. WO 03/0872292). The product formats are:

Cell therapy bioreactor—In one representation, there is a vial contained within the overall bioreactor (FIG. 8C) where the vial enables cell sedimentation. After cell sedimentation the design of the cell therapy bioreactor provides for the removal of the media supernatant leaving the concentrated cells in a small cone at the base of the vial. This approach provides a vial with concentrated cells as is now provided by centralized cell therapy providers. With this automated technique, additional use of a centrifuge to concentrate the cells at the end of the process as per conventional manual techniques is not required.

Single (TE) tissue engineered bioreactor—The bioreactor facilitating all ports at the top for easy connection with the system via needleless connectors (FIGS. 7B and 8B). The approach to the formation of the tissue engineered implant is similar to that described in Applicant's International Patent Application No. WO 03/0872292)

Multiple (TE) tissue engineered implants—This is similar to that defined in the Applicant's International Patent Application No. WO 03/0872292.

Cell matrix Implant bioreactor—This is a hybrid of cell therapy and tissue engineering where cells are cultured for a short period on a matrix to allow attachment but minimal tissue formation. The cell matrix may be flexible. This technique has been references as MACI approach (matrix Induced autologous chondrocyte implantation).

The product bioreactor (in any of the aforementioned formats) also benefits from the twin "containment layers" (as shown in FIGS. 7A, 7B, 8A, and 8B) as substantially employed for the tissue digestion bioreactor. In the case of a product bioreactor, the value of the twin layers (i.e. the outer containment unit) is to allow the bioreactor contained therein to be disassembled in a sequence consistent with operating room practice. That is to say that the exterior can be removed and the interior parts handled while maintaining aseptic practices.

Other Components

Beyond the different bioreactor chamber assemblies that incorporate the double containment system, a high efficiency cross-flow filter can be implemented to enable cell concentration post proliferation collection. This component eliminates centrifugation. This component Is shown in the flow diagram (FIG. 13).

In, aspects, a space and cost efficient valve manifold has been designed that provides the fluid management described in the Applicant's International Patent Application No. WO 03/0872292 while also providing the structural support for the valve array, the critical fluid interconnects between the valves the bioreactors and the fluid reservoir, and the attachment points for the tissue engineering module latches.

A cell collection reservoir has been included in the design as a staging area and to allow for warming of fluid from the reservoir prior to infusion into the different chamber assemblies.

Although preferred embodiments have been described herein, it is understood by one of skill in the art that variations may be made thereto without departing from the spirit of the invention.

We claim:

1. A tissue engineering module comprising:
   a housing supporting at least one chamber assembly, said at least one chamber assembly selected for at least one of tissue digestion, cell proliferation, cell differentiation and implant formation;
   a fluid reservoir operationally engageable with the housing and comprising as internal elements a set of flexible bags that are used to contain all of the processing fluids and waste fluids for automated flow to and from said at least one chamber assembly, wherein the fluid reservoir operates at reduced temperature from the housing to keep fluids viable for extended periods by local active temperature control of at least one bag, and wherein said fluid reservoir is operationally engaged with a collection reservoir to allow for warming of fluid from said fluid reservoir prior to introduction into said at least one chamber assembly; and at least one biosensor for the monitoring of parameters of the fluid reservoir and cells and/or tissues within at least one chamber assembly, said at least one biosensor relaying variable parameter information to a microprocessor to process the parameters and dynamically adjust and adapt to specific needs of cells and/or tissues during tissue digestion, cell proliferation, cell differentiation and/or implant formation.

2. The tissue engineering module of claim 1, wherein the tissue engineering module is capable of conducting at least one of tissue digestion, cell proliferation, cell differentiation and implant formation; individually, sequentially, in predetermined sequences or partial sequences.

3. The tissue engineering module of claim 1, wherein at least two chamber assemblies are operatively connected.

4. The tissue engineering module of claim 3, wherein said at least two chambers are at least one of independently operable and co-operatively operable.

5. The tissue engineering module of claim 3, wherein said at least two chamber assemblies are operatively connected to provide for the exchange of at least one of fluids, cells and tissues between said chambers.

6. The tissue engineering module of claim 3, wherein said at least two chambers are connected via at least one of a passageway, tubing, connector, valve, pump, filter, fluid access port, in-line gas exchange membrane, and in-line sensor.

7. The tissue engineering module of claim 1, wherein said at least one chamber assembly provides an environment for at least one of the following selected from the group consisting of storage of tissue biopsy, digestion of tissue biopsy, cell sorting, cell washing, cell concentrating, cell seeding, cell proliferation, cell differentiation, cell storage, cell transport, tissue formation, implant formation, storage of implantable tissue and transport of implantable tissue.

8. The tissue engineering module of claim 1, wherein the module provides the formation of cells and/or tissues on and/or within at least one of a scaffold, membrane and matrix.

9. The tissue engineering module of claim 1, wherein the cells and tissues are selected from bone, cartilage, cardiac tissue, vascular implants, skin grafts, tendon, disc, related bone and cartilage precursor cells and combinations thereof.

10. The tissue engineering module of claim 1, wherein the fluid reservoir comprises connectors and the housing further comprises mating connectors, the connectors of the fluid reservoir engaging the mating connectors of the housing.

11. The tissue engineering module of claim 10, wherein the connectors of the fluid reservoir are in fluid communion with the mating connectors of the housing.

12. The tissue engineering module of claim 1, wherein the fluid reservoir is operationally engageable with the housing via a one-way snap-on connection.

13. The tissue engineering module of claim 1, wherein the fluid reservoir comprises a double walled reservoir with an air space between the two walls.

14. The tissue engineering module of claim 1, wherein the fluid reservoir is pre-filled.

15. The tissue engineering module of claim 1, wherein the fluid reservoir comprises at least one hole for receiving a temperature controller to control the temperature of said at least one bag.

16. The tissue engineering module of claim 1, wherein at least one of said at least one chamber assembly is engageable with the housing.

17. The tissue engineering module of claim 16, wherein at least one of said at least one chamber assembly is reversibly engageable with a tissue engineering module.

18. The tissue engineering module of claim 1, wherein said at least one biosensor has the ability to monitor the specific performance of cell populations/tissue in said at least one chamber assembly from various donors and thereby, allow the system to accommodate for the requirements of cells/tissue of individual donors in said at least one chamber assembly.

19. The tissue engineering module of claim 1, wherein the housing further comprises at least one additional chamber assembly that can share a common process with an existing chamber assembly such that the additional chamber assembly can be removed in order to provide analysis and/or evaluation of the contents of the chamber that parallels the contents of the existing chamber.

20. The tissue engineering module of claim 19, wherein the contents are media, tissue and/or cells.

21. The tissue engineering module of claim 1, wherein at least one of said at least one chamber assembly comprises at least one of a tissue digestion chamber assembly, a proliferation chamber assembly and a product chamber assembly.

22. The tissue engineering module of claim 21, wherein the fluid reservoir is in fluid communication with said at least one of the tissue digestion chamber assembly, the proliferation chamber assembly and the product chamber assembly.

23. The tissue engineering module of claim 21, wherein said at least one chamber assembly comprises the tissue digestion chamber assembly, the proliferation chamber assembly and the product chamber assembly.

24. The tissue engineering module of claim 21, wherein said at least one biosensor is associated with at least one of the fluid reservoir, the tissue digestion chamber assembly, the proliferation chamber assembly and the product chamber assembly, said at least one biosensor being in communication with a microprocessor.

25. The tissue engineering module of claim 21, wherein at least one of the tissue digestion chamber assembly, the proliferation chamber assembly, and the product chamber assembly is mountable in the housing.

26. The tissue engineering module of claim 21, wherein at least one of the tissue digestion chamber assembly, the proliferation chamber assembly, and the product chamber assembly is portable.

27. The tissue engineering module of claim 21, wherein at least one of the tissue digestion chamber assembly, the proliferation chamber assembly, and the product chamber assembly is removable from the housing.

28. The tissue engineering module of claim 21, wherein the tissue digestion chamber assembly and the product chamber assembly are removable from the housing and the proliferation chamber assembly is fixed to the housing.

29. The tissue engineering module of claim 21, wherein the tissue digestion chamber assembly is for receiving patient cells, with or without the need for digestion.

30. The tissue engineering module of claim 21, wherein the tissue digestion chamber assembly comprises a tissue digestion bioreactor, the proliferation chamber assembly comprises a proliferation bioreactor, and the product chamber assembly comprises a product bioreactor.

31. The tissue engineering module of claim 21, wherein the tissue digestion chamber assembly comprises:
    a protective containment unit comprising a unit lid and a unit base; and a tissue digestion bioreactor within the protective containment unit.

32. The tissue engineering module of claim 21, wherein the tissue digestion bioreactor comprises a tissue digestion chamber and a removable bioreactor lid connected to the tissue digestion chamber, the removable bioreactor lid having at least one port in fluid communion with the tissue digestion chamber.

33. The tissue engineering module of claim 32, wherein the tissue digestion chamber comprises a port filter.

34. The tissue engineering module of claim 32, wherein said at least one port comprises a port filter.

35. The tissue engineering module of claim 21, wherein the proliferation chamber assembly comprises:
   a proliferation bioreactor comprising a proliferation chamber having a base, a lid for containment of fluid, and a channel system therein.

36. The tissue engineering module of claim 35, wherein the base is mounted within the proliferation chamber at an angle to provide an elevational change from an inlet to an outlet.

37. The tissue engineering module of claim 35, wherein the base is substantially flat.

38. The tissue engineering module of claim 35, wherein the proliferation chamber has more than one base stacked on top of one another to provide additional surface area for the proliferation of cells.

39. The tissue engineering module of claim 35, wherein the channel system is for flow of medium and cells.

40. The tissue engineering module of claim 35, wherein the proliferation bioreactor has at least one biosensor to detect and provide feedback on the condition of cell culture and proliferative activity.

41. The tissue engineering module of claim 35, wherein the proliferation bioreactor further comprises at least one of a gas permeable membrane, flow interrupters, and vibratory elements.

42. The tissue engineering module of claim 21, wherein the product chamber assembly comprises:
   a protective containment unit comprising a unit lid and a unit base; and
   a product bioreactor supported within the protective containment unit.

43. The tissue engineering module of claim 42, wherein the product bioreactor is one of a cell therapy bioreactor or a differentiation bioreactor.

44. The tissue engineering module of claim 43, wherein the cell therapy bioreactor collects and holds proliferated cells for cell therapy applications.

45. The tissue engineering module of claim 43, wherein the differentiation bioreactor is configured for at least one of the collection of cells, the generation of a cell implant, and the generation of a tissue implant.

46. An automated tissue engineering system comprising:
   at least one tissue engineering module of claim 1, supported within a housing; and
   a central microprocessor that controls functioning of said at least one tissue engineering module.

47. The automated tissue engineering system of claim 46, wherein at least one biosensor is associated with at least one of the housing and said at least one tissue engineering module.

48. The automated tissue engineering system of claim 46, wherein the tissue engineering system is capable of conducting at least one of tissue digestion, cell proliferation, cell differentiation and implant formation; individually, sequentially, in predetermined sequences or partial sequences.

49. A network of automated tissue engineering systems, wherein at least one of the automated tissue engineering systems is the automated tissue engineering system of claim 46.

50. A tissue engineering module comprising:
   a detachable fluid reservoir comprising at least one of:
   (a) a tissue digestion bioreactor;
   (b) a proliferation bioreactor; or
   (c) a product bioreactor; and
   at least one biosensor for the monitoring of variable parameters of the fluid reservoir and said at least one bioreactor of (a), (b) or (c),
   wherein the fluid reservoir further comprises as internal elements a set of flexible bags that are used to contain all of the processing fluids and waste fluids, wherein the fluid reservoir is configured to permit local active temperature control of at least one bag at about less than 37° C. to keep fluids viable for extended periods, and wherein said fluid reservoir is engaged with a collection reservoir to allow for warming of fluid from said fluid reservoir prior to introduction into at least one bioreactor of (a), (b) or (c);
   further wherein said at least one biosensor relays variable parameter information of cells and/or tissues in said at least one bioreactor of (a), (b) or (c) to a microprocessor to process the parameters and dynamically adjust the parameters accordingly to needs of said cells and/or tissues.

51. The tissue engineering module of claim 50, wherein the tissue engineering module is capable of conducting at least one of tissue digestion, cell proliferation, cell differentiation and implant formation; individually, sequentially, in predetermined sequences or partial sequences.

52. The tissue engineering module of claim 50, wherein at least two chamber assemblies are operatively connected.

53. The tissue engineering module of claim 52, wherein said at least two chambers are at least one of independently operable and co-operatively operable.

54. The tissue engineering module of claim 52, wherein said at least two chamber assemblies are operatively connected to provide for the exchange of at least one of fluids, cells and tissues between said chambers.

55. The tissue engineering module of claim 52, wherein said at least two chambers are connected via at least one of a passageway, tubing, connector, valve, pump, filter, fluid access port, in-line gas exchange membrane, and in-line sensor.

* * * * *